(12) United States Patent
Bonutti

(10) Patent No.: US 9,999,449 B2
(45) Date of Patent: Jun. 19, 2018

(54) DEVICES AND METHODS FOR STABILIZING TISSUE AND IMPLANTS

(71) Applicant: P Tech, LLC, Effingham, IL (US)

(72) Inventor: Peter M. Bonutti, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 555 days.

(21) Appl. No.: 14/205,442

(22) Filed: Mar. 12, 2014

(65) Prior Publication Data

US 2014/0194989 A1 Jul. 10, 2014

Related U.S. Application Data

(63) Continuation of application No. 11/258,795, filed on Oct. 26, 2005.
(Continued)

(51) Int. Cl.
| | | |
|---|---|---|
| A61F 2/44 | (2006.01) |
| A61B 17/70 | (2006.01) |
| A61F 2/30 | (2006.01) |
| A61L 27/58 | (2006.01) |
| A61F 2/08 | (2006.01) |

(Continued)

(52) U.S. Cl.
CPC ...... *A61B 17/7064* (2013.01); *A61B 17/0401* (2013.01); *A61B 17/7067* (2013.01); *A61F 2/08* (2013.01); *A61F 2/0811* (2013.01); *A61F 2/30749* (2013.01); *A61F 2/441* (2013.01); *A61F 2/442* (2013.01); *A61F 2/4405* (2013.01); *A61L 27/58* (2013.01); *A61B 17/842* (2013.01); *A61B 2017/00398* (2013.01); *A61B 2017/00951* (2013.01); *A61B 2017/0404* (2013.01); *A61B 2017/0496* (2013.01); *A61B 2090/064* (2016.02); *A61F 2/0063* (2013.01);
(Continued)

(58) Field of Classification Search
CPC ...... A61B 17/0401; A61F 2/08; A61F 2/0811; A61F 2/30749; A61F 2/30751
USPC ..................... 606/228–233; 623/13.11–13.19
See application file for complete search history.

(56) References Cited

U.S. PATENT DOCUMENTS

| | | |
|---|---|---|
| 319,296 A | 6/1885 | Molesworth |
| 668,878 A | 2/1901 | Jensen |

(Continued)

FOREIGN PATENT DOCUMENTS

| | | |
|---|---|---|
| CA | 2641580 A1 | 8/2007 |
| CA | 2680827 A1 | 9/2008 |

(Continued)

OTHER PUBLICATIONS

Office Action dated Jun. 27, 2014 in U.S. Appl. No. 14/032,969.
(Continued)

*Primary Examiner* — Matthew Lawson
(74) *Attorney, Agent, or Firm* — Senniger Powers LLP

(57) ABSTRACT

An implant for repairing a joint between a first bone and a second bone includes a first section constructed of a substantially rigid material and a graft constructed of soft tissue having a first end and a second end. The first section has a first end surface configured for positioning against the first bone. The graft is configured for stabilizing the first section relative to the first bone. A first fastener is configured for mounting to the graft and the first section to anchor the graft to the first section. A second fastener is configured for mounting to the graft and the first bone to anchor the graft to the first bone.

12 Claims, 10 Drawing Sheets

Related U.S. Application Data

(60) Provisional application No. 60/622,095, filed on Oct. 26, 2004.

(51) Int. Cl.
*A61B 17/04* (2006.01)
*A61B 90/00* (2016.01)
*A61F 2/00* (2006.01)
*A61B 17/84* (2006.01)
*A61B 17/00* (2006.01)

(52) U.S. Cl.
CPC ............... *A61F 2002/30462* (2013.01); *A61F 2002/4435* (2013.01)

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 6/1938 | Hanicke |
| 2,178,840 A | 11/1939 | Lorenian |
| 2,187,852 A | 1/1940 | Friddle |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston |
| 3,518,993 A | 7/1970 | Blake |
| 3,577,991 A | 5/1971 | Wilkinson |
| 3,596,292 A | 8/1971 | Erb et al. |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston et al. |
| 3,678,980 A | 7/1972 | Gutshall |
| 3,709,218 A | 1/1973 | Halloran |
| 3,711,347 A | 1/1973 | Wagner et al. |
| 3,760,808 A | 9/1973 | Bleuer |
| 3,788,318 A | 1/1974 | Kim et al. |
| 3,789,852 A | 2/1974 | Kim et al. |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee et al. |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold et al. |
| 3,898,992 A | 8/1975 | Balamuth |
| 3,918,442 A | 11/1975 | Nikolaev et al. |
| 3,968,800 A | 7/1976 | Vilasi |
| 4,023,559 A | 5/1977 | Gaskell |
| 4,064,566 A | 12/1977 | Fletcher et al. |
| 4,089,071 A | 5/1978 | Kalnberz et al. |
| 4,156,574 A | 5/1979 | Boden |
| 4,164,794 A | 8/1979 | Spector et al. |
| 4,171,544 A | 10/1979 | Hench et al. |
| 4,183,102 A | 1/1980 | Guiset et al. |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,226,228 A | 10/1980 | Shin |
| 4,235,233 A | 11/1980 | Mouwen |
| 4,235,238 A | 11/1980 | Ogiu et al. |
| 4,257,411 A | 3/1981 | Cho |
| 4,265,231 A | 5/1981 | Scheller, Jr. et al. |
| 4,281,649 A | 8/1981 | Derweduwen |
| 4,291,698 A | 9/1981 | Fuchs |
| 4,309,488 A | 1/1982 | Heide et al. |
| 4,320,762 A | 3/1982 | Bentov |
| 4,351,069 A | 9/1982 | Ballintyn et al. |
| 4,364,381 A | 12/1982 | Sher et al. |
| 4,365,356 A | 12/1982 | Broemer et al. |
| 4,388,921 A | 6/1983 | Sutter et al. |
| 4,395,798 A | 8/1983 | McVey |
| 4,409,974 A | 10/1983 | Freedland |
| 4,414,166 A | 11/1983 | Charlson et al. |
| 4,437,191 A | 3/1984 | van der Zel et al. |
| 4,437,362 A | 3/1984 | Hurst |
| 4,444,180 A | 4/1984 | Schneider et al. |
| 4,448,194 A | 5/1984 | DiGiovanni et al. |
| 4,456,005 A | 6/1984 | Lichty |
| 4,461,281 A | 7/1984 | Carson |
| 4,493,317 A | 1/1985 | Klaue |
| 4,495,664 A | 1/1985 | Blanquaert |
| 4,501,031 A | 2/1985 | McDaniel et al. |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins et al. |
| 4,556,350 A | 12/1985 | Bernhardt et al. |
| 4,566,138 A | 1/1986 | Lewis et al. |
| 4,589,868 A | 5/1986 | Dretler |
| 4,590,928 A * | 5/1986 | Hunt .................... A61B 17/686 606/327 |
| 4,597,379 A | 7/1986 | Kihn et al. |
| 4,599,085 A | 7/1986 | Riess et al. |
| 4,601,893 A | 7/1986 | Cardinal |
| 4,606,335 A | 8/1986 | Wedeen |
| 4,621,640 A | 11/1986 | Mulhollan et al. |
| 4,630,609 A | 12/1986 | Chin |
| 4,632,101 A | 12/1986 | Freedland |
| 4,645,503 A | 2/1987 | Lin et al. |
| 4,657,460 A | 4/1987 | Bien |
| 4,659,268 A | 4/1987 | Del Mundo et al. |
| 4,662,063 A | 5/1987 | Collins et al. |
| 4,662,068 A | 5/1987 | Polonsky |
| 4,662,887 A | 5/1987 | Turner et al. |
| 4,669,473 A | 6/1987 | Richards et al. |
| 4,685,458 A | 8/1987 | Leckrone |
| 4,691,741 A | 9/1987 | Affa et al. |
| 4,705,040 A | 11/1987 | Mueller et al. |
| 4,706,670 A | 11/1987 | Andersen et al. |
| 4,708,139 A | 11/1987 | Dunbar, IV |
| 4,713,077 A | 12/1987 | Small |
| 4,716,901 A | 1/1988 | Jackson et al. |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble et al. |
| 4,739,751 A | 4/1988 | Sapega et al. |
| 4,741,330 A | 5/1988 | Hayhurst |
| 4,749,585 A | 6/1988 | Greco et al. |
| 4,750,492 A | 6/1988 | Jacobs |
| 4,768,507 A | 9/1988 | Fischell et al. |
| 4,772,286 A | 9/1988 | Goble et al. |
| 4,776,328 A | 10/1988 | Frey et al. |
| 4,776,738 A | 10/1988 | Winston |
| 4,776,851 A | 10/1988 | Bruchman et al. |
| 4,781,182 A | 11/1988 | Purnell et al. |
| 4,790,303 A | 12/1988 | Steffee |

(56) References Cited

U.S. PATENT DOCUMENTS

| | | |
|---|---|---|
| 4,792,336 A | 12/1988 | Hlavacek et al. |
| 4,817,591 A | 4/1989 | Klaue |
| 4,822,224 A | 4/1989 | Carl et al. |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart et al. |
| 4,846,812 A | 7/1989 | Walker et al. |
| 4,862,882 A | 9/1989 | Venturi et al. |
| 4,869,242 A | 9/1989 | Galluzzo |
| 4,870,957 A | 10/1989 | Goble et al. |
| 4,883,048 A | 11/1989 | Purnell et al. |
| 4,890,612 A | 1/1990 | Kensey |
| 4,895,148 A | 1/1990 | Bays et al. |
| 4,898,156 A | 2/1990 | Gatturna et al. |
| 4,899,729 A | 2/1990 | Gill et al. |
| 4,899,744 A | 2/1990 | Fujitsuka et al. |
| 4,901,721 A | 2/1990 | Hakki |
| 4,921,479 A | 5/1990 | Grayzel |
| 4,922,897 A | 5/1990 | Sapega et al. |
| 4,924,866 A | 5/1990 | Yoon |
| 4,932,960 A | 6/1990 | Green et al. |
| 4,935,026 A | 6/1990 | McFadden |
| 4,935,028 A | 6/1990 | Drews |
| 4,945,625 A | 8/1990 | Winston |
| 4,946,468 A | 8/1990 | Li |
| 4,954,126 A | 9/1990 | Wallsten |
| 4,955,910 A | 9/1990 | Bolesky |
| 4,957,498 A | 9/1990 | Caspari et al. |
| 4,961,741 A | 10/1990 | Hayhurst |
| 4,963,151 A | 10/1990 | Ducheyne et al. |
| 4,966,583 A | 10/1990 | Debbas |
| 4,968,315 A | 11/1990 | Gatturna |
| 4,969,888 A | 11/1990 | Scholten |
| 4,969,892 A | 11/1990 | Burton et al. |
| 4,990,161 A | 2/1991 | Kampner |
| 4,994,071 A | 2/1991 | MacGregor |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka et al. |
| 5,009,652 A | 4/1991 | Morgan et al. |
| 5,009,663 A | 4/1991 | Broome |
| 5,009,664 A | 4/1991 | Sievers |
| 5,013,316 A | 5/1991 | Goble et al. |
| 5,019,090 A | 5/1991 | Pinchuk |
| 5,021,059 A | 6/1991 | Kensey et al. |
| 5,035,713 A | 7/1991 | Friis |
| 5,037,404 A | 8/1991 | Gold et al. |
| 5,037,422 A | 8/1991 | Hayhurst et al. |
| 5,041,093 A | 8/1991 | Chu |
| 5,041,114 A | 8/1991 | Chapman et al. |
| 5,041,129 A | 8/1991 | Hayhurst et al. |
| 5,046,513 A | 9/1991 | Gatturna et al. |
| 5,047,055 A | 9/1991 | Bao et al. |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot et al. |
| 5,078,731 A | 1/1992 | Hayhurst |
| 5,078,744 A | 1/1992 | Chvapil |
| 5,078,745 A | 1/1992 | Rhenter et al. |
| 5,084,050 A | 1/1992 | Draenert |
| 5,084,051 A | 1/1992 | Tormala et al. |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante et al. |
| 5,100,405 A | 3/1992 | McLaren |
| 5,100,417 A | 3/1992 | Cerier et al. |
| 5,102,417 A | 4/1992 | Palmaz |
| 5,102,421 A | 4/1992 | Anspach, Jr. |
| 5,108,399 A | 4/1992 | Eitenmuller et al. |
| 5,120,175 A | 6/1992 | Arbegast et al. |
| 5,123,520 A | 6/1992 | Schmid et al. |
| 5,123,914 A | 6/1992 | Cope |
| 5,123,941 A | 6/1992 | Lauren et al. |
| 5,133,732 A | 7/1992 | Wiktor |
| RE34,021 E | 8/1992 | Mueller et al. |
| 5,141,520 A | 8/1992 | Goble et al. |
| 5,147,362 A | 9/1992 | Goble |
| 5,152,790 A * | 10/1992 | Rosenberg ............ A61F 2/0811 606/304 |
| 5,154,720 A | 10/1992 | Trott et al. |
| 5,156,613 A | 10/1992 | Sawyer |
| 5,156,616 A | 10/1992 | Meadows et al. |
| 5,158,566 A | 10/1992 | Pianetti |
| 5,158,934 A | 10/1992 | Ammann et al. |
| 5,163,960 A | 11/1992 | Bonutti |
| 5,171,251 A | 12/1992 | Bregen et al. |
| 5,176,682 A | 1/1993 | Chow |
| 5,179,964 A | 1/1993 | Cook |
| 5,180,388 A | 1/1993 | DiCarlo |
| 5,183,464 A | 2/1993 | Dubrul et al. |
| 5,192,287 A | 3/1993 | Fournier et al. |
| 5,192,326 A | 3/1993 | Bao et al. |
| 5,197,166 A | 3/1993 | Meier et al. |
| 5,197,971 A | 3/1993 | Bonutti |
| 5,203,784 A | 4/1993 | Ross et al. |
| 5,203,787 A | 4/1993 | Noblitt |
| 5,208,950 A | 5/1993 | Merritt |
| 5,209,776 A | 5/1993 | Bass et al. |
| 5,217,493 A | 6/1993 | Raad et al. |
| 5,219,359 A | 6/1993 | McQuilkin et al. |
| 5,226,899 A | 7/1993 | Lee et al. |
| 5,234,006 A | 8/1993 | Eaton et al. |
| 5,234,425 A | 8/1993 | Fogarty et al. |
| 5,236,438 A | 8/1993 | Wilk |
| 5,236,445 A | 8/1993 | Hayhurst et al. |
| 5,242,902 A | 9/1993 | Murphy et al. |
| 5,254,113 A | 10/1993 | Wilk |
| 5,258,007 A | 11/1993 | Spetzler et al. |
| 5,258,015 A | 11/1993 | Li et al. |
| 5,258,016 A | 11/1993 | DiPoto et al. |
| 5,266,325 A | 11/1993 | Kuzma et al. |
| 5,269,783 A | 12/1993 | Sander |
| 5,269,785 A | 12/1993 | Bonutti |
| 5,269,809 A | 12/1993 | Hayhurst et al. |
| 5,281,235 A | 1/1994 | Haber et al. |
| 5,282,832 A | 2/1994 | Toso et al. |
| 5,290,281 A | 3/1994 | Tschakaloff |
| 5,304,119 A | 4/1994 | Balaban et al. |
| 5,306,280 A | 4/1994 | Bregen et al. |
| 5,306,301 A | 4/1994 | Graf et al. |
| 5,315,741 A | 5/1994 | Dubberke |
| 5,318,588 A | 6/1994 | Horzewski et al. |
| 5,320,611 A | 6/1994 | Bonutti et al. |
| 5,324,308 A | 6/1994 | Pierce |
| 5,328,480 A | 7/1994 | Melker et al. |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot et al. |
| 5,330,486 A | 7/1994 | Wilk |
| 5,336,231 A | 8/1994 | Adair |
| 5,336,240 A | 8/1994 | Metzler et al. |
| 5,339,799 A | 8/1994 | Kami et al. |
| 5,349,956 A | 9/1994 | Bonutti |
| 5,352,229 A | 10/1994 | Goble et al. |
| 5,354,298 A | 10/1994 | Lee et al. |
| 5,354,302 A | 10/1994 | Ko |
| 5,366,480 A | 11/1994 | Corriveau et al. |
| 5,370,646 A | 12/1994 | Reese et al. |
| 5,370,660 A | 12/1994 | Weinstein et al. |
| 5,372,146 A | 12/1994 | Branch |
| 5,374,235 A | 12/1994 | Ahrens |
| 5,376,126 A | 12/1994 | Lin |

(56) References Cited

U.S. PATENT DOCUMENTS

| | | |
|---|---|---|
| 5,382,254 A | 1/1995 | McGarry et al. |
| 5,383,883 A | 1/1995 | Wilk et al. |
| 5,383,905 A | 1/1995 | Golds et al. |
| 5,391,173 A | 2/1995 | Wilk |
| 5,395,308 A | 3/1995 | Fox et al. |
| 5,397,311 A | 3/1995 | Walker et al. |
| 5,400,805 A | 3/1995 | Warren |
| 5,403,312 A | 4/1995 | Yates et al. |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker et al. |
| 5,423,796 A | 6/1995 | Shikhman et al. |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr et al. |
| 5,447,503 A | 9/1995 | Miller |
| 5,449,372 A | 9/1995 | Schmaltz et al. |
| 5,449,382 A | 9/1995 | Dayton |
| 5,451,235 A | 9/1995 | Lock et al. |
| 5,453,090 A | 9/1995 | Martinez et al. |
| 5,456,722 A | 10/1995 | McLeod et al. |
| 5,458,653 A | 10/1995 | Davidson |
| 5,462,561 A | 10/1995 | Voda |
| 5,464,424 A | 11/1995 | O'Donnell, Jr. |
| 5,464,426 A | 11/1995 | Bonutti |
| 5,464,427 A | 11/1995 | Curtis et al. |
| 5,470,337 A | 11/1995 | Moss |
| 5,472,444 A | 12/1995 | Huebner et al. |
| 5,474,554 A | 12/1995 | Ku |
| 5,478,351 A | 12/1995 | Meade et al. |
| 5,478,353 A | 12/1995 | Yoon |
| 5,480,403 A | 1/1996 | Lee et al. |
| 5,486,197 A | 1/1996 | Le et al. |
| 5,487,844 A | 1/1996 | Fujita |
| 5,488,958 A | 2/1996 | Topel et al. |
| 5,496,292 A | 3/1996 | Burnham |
| 5,496,318 A | 3/1996 | Howland |
| 5,496,335 A | 3/1996 | Thomason et al. |
| 5,496,348 A | 3/1996 | Bonutti |
| 5,500,000 A | 3/1996 | Feagin et al. |
| 5,501,700 A | 3/1996 | Hirata |
| 5,504,977 A | 4/1996 | Weppner et al. |
| 5,505,735 A | 4/1996 | Li |
| 5,507,754 A | 4/1996 | Green et al. |
| 5,522,844 A | 6/1996 | Johnson |
| 5,522,845 A | 6/1996 | Wenstrom, Jr. |
| 5,522,846 A | 6/1996 | Bonutti |
| 5,527,341 A | 6/1996 | Gogolewski et al. |
| 5,527,342 A | 6/1996 | Pietrzak et al. |
| 5,527,343 A | 6/1996 | Bonutti |
| 5,529,075 A | 6/1996 | Clark |
| 5,531,759 A | 7/1996 | Kensey et al. |
| 5,534,012 A | 7/1996 | Bonutti |
| 5,534,028 A | 7/1996 | Bao et al. |
| 5,540,718 A | 7/1996 | Bartlett |
| 5,542,423 A | 8/1996 | Bonutti |
| 5,545,178 A | 8/1996 | Kensey et al. |
| 5,545,180 A | 8/1996 | Le et al. |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin et al. |
| 5,569,305 A | 10/1996 | Bonutti |
| 5,569,306 A | 10/1996 | Thal |
| 5,573,517 A | 11/1996 | Bonutti et al. |
| 5,573,538 A | 11/1996 | Laboureau |
| 5,573,542 A | 11/1996 | Stevens |
| 5,575,801 A | 11/1996 | Habermeyer et al. |
| 5,580,344 A | 12/1996 | Hasson |
| 5,584,835 A | 12/1996 | Greenfield |
| 5,584,860 A | 12/1996 | Goble et al. |
| 5,584,862 A | 12/1996 | Bonutti |
| 5,591,206 A | 1/1997 | Moufarrege |
| 5,593,422 A | 1/1997 | Muijs Van De Moer |
| 5,593,425 A | 1/1997 | Bonutti et al. |
| 5,593,625 A | 1/1997 | Riebel et al. |
| 5,601,557 A | 2/1997 | Hayhurst |
| 5,601,558 A | 2/1997 | Torrie et al. |
| 5,601,595 A | 2/1997 | Smith |
| 5,607,427 A | 3/1997 | Tschakaloff |
| 5,609,595 A | 3/1997 | Pennig |
| 5,618,314 A | 4/1997 | Harwin et al. |
| 5,620,461 A | 4/1997 | Muijs Van De Moer et al. |
| 5,626,612 A | 5/1997 | Bartlett |
| 5,626,614 A | 5/1997 | Hart |
| 5,626,718 A | 5/1997 | Philippe et al. |
| 5,628,751 A | 5/1997 | Sander et al. |
| 5,630,824 A | 5/1997 | Hart |
| 5,634,926 A | 6/1997 | Jobe |
| 5,643,274 A | 7/1997 | Sander et al. |
| 5,643,293 A | 7/1997 | Kogasaka et al. |
| 5,643,295 A | 7/1997 | Yoon |
| 5,643,321 A | 7/1997 | McDevitt |
| 5,645,553 A | 7/1997 | Kolesa et al. |
| 5,645,597 A | 7/1997 | Krapiva |
| 5,645,599 A | 7/1997 | Samani |
| 5,649,955 A | 7/1997 | Hashimoto et al. |
| 5,649,963 A | 7/1997 | McDevitt |
| 5,651,377 A | 7/1997 | O'Donnell, Jr. |
| 5,658,313 A | 8/1997 | Thal |
| 5,660,225 A | 8/1997 | Saffran |
| 5,662,658 A | 9/1997 | Wenstrom, Jr. |
| 5,665,089 A | 9/1997 | Dall et al. |
| 5,665,109 A | 9/1997 | Yoon |
| 5,667,513 A | 9/1997 | Torrie et al. |
| 5,669,917 A | 9/1997 | Sauer et al. |
| 5,674,240 A | 10/1997 | Bonutti et al. |
| 5,681,310 A | 10/1997 | Yuan et al. |
| 5,681,333 A | 10/1997 | Burkhart et al. |
| 5,681,351 A | 10/1997 | Jamiolkowski et al. |
| 5,681,352 A | 10/1997 | Clancy, III et al. |
| 5,685,820 A | 11/1997 | Riek et al. |
| 5,688,283 A | 11/1997 | Knapp |
| 5,690,654 A | 11/1997 | Ovil |
| 5,690,655 A | 11/1997 | Hart et al. |
| 5,690,676 A | 11/1997 | DiPoto et al. |
| 5,693,055 A | 12/1997 | Zahiri et al. |
| 5,697,950 A | 12/1997 | Fucci et al. |
| 5,702,397 A | 12/1997 | Goble et al. |
| 5,702,422 A * | 12/1997 | Stone ............... A61B 17/0401 606/232 |
| 5,702,462 A | 12/1997 | Oberlander |
| 5,707,395 A | 1/1998 | Li |
| 5,713,903 A | 2/1998 | Sander et al. |
| 5,713,921 A | 2/1998 | Bonutti |
| 5,718,717 A | 2/1998 | Bonutti |
| 5,720,747 A | 2/1998 | Burke |
| 5,720,753 A | 2/1998 | Sander et al. |
| 5,725,541 A | 3/1998 | Anspach, III et al. |
| 5,725,556 A | 3/1998 | Moser et al. |
| 5,725,582 A | 3/1998 | Bevan et al. |
| 5,730,747 A | 3/1998 | Ek et al. |
| 5,733,306 A | 3/1998 | Bonutti |
| 5,735,875 A | 4/1998 | Bonutti et al. |
| 5,735,877 A | 4/1998 | Pagedas |
| 5,735,899 A | 4/1998 | Schwartz et al. |
| 5,741,282 A | 4/1998 | Anspach, III et al. |
| 5,752,952 A | 5/1998 | Adamson |
| 5,752,974 A | 5/1998 | Rhee et al. |
| 5,755,809 A | 5/1998 | Cohen et al. |
| 5,762,458 A | 6/1998 | Wang et al. |
| 5,766,221 A | 6/1998 | Benderev et al. |
| 5,769,894 A | 6/1998 | Ferragamo |
| 5,772,672 A | 6/1998 | Toy et al. |
| 5,776,151 A | 7/1998 | Chan |
| 5,779,706 A | 7/1998 | Tschakaloff |
| 5,782,862 A | 7/1998 | Bonutti |
| 5,785,713 A | 7/1998 | Jobe |

(56) References Cited

U.S. PATENT DOCUMENTS

| | | |
|---|---|---|
| 5,792,096 A | 8/1998 | Rentmeester et al. |
| 5,797,931 A | 8/1998 | Bito et al. |
| 5,800,537 A | 9/1998 | Bell |
| 5,807,403 A | 9/1998 | Beyar et al. |
| 5,810,849 A | 9/1998 | Kontos |
| 5,810,853 A | 9/1998 | Yoon |
| 5,810,884 A | 9/1998 | Kim |
| 5,811,721 A | 9/1998 | Andersson et al. |
| 5,814,072 A | 9/1998 | Bonutti |
| 5,814,073 A | 9/1998 | Bonutti |
| 5,817,107 A | 10/1998 | Schaller |
| 5,823,994 A | 10/1998 | Sharkey et al. |
| 5,824,009 A | 10/1998 | Fukuda et al. |
| 5,830,125 A | 11/1998 | Scribner et al. |
| 5,836,897 A | 11/1998 | Sakurai et al. |
| 5,839,899 A | 11/1998 | Robinson |
| 5,843,178 A | 12/1998 | Vanney et al. |
| 5,845,645 A | 12/1998 | Bonutti |
| 5,851,185 A | 12/1998 | Berns |
| 5,865,834 A | 2/1999 | McGuire |
| 5,866,634 A | 2/1999 | Tokushige et al. |
| 5,868,749 A | 2/1999 | Reed |
| 5,874,235 A | 2/1999 | Chan |
| 5,879,372 A | 3/1999 | Bartlett |
| 5,891,166 A | 4/1999 | Schervinsky |
| 5,891,168 A | 4/1999 | Thal |
| 5,893,880 A | 4/1999 | Egan et al. |
| 5,897,574 A | 4/1999 | Bonutti |
| 5,899,911 A | 5/1999 | Carter |
| 5,899,921 A | 5/1999 | Caspari et al. |
| 5,906,579 A | 5/1999 | Vander Salm et al. |
| 5,906,625 A | 5/1999 | Bito et al. |
| 5,908,429 A | 6/1999 | Yoon |
| 5,911,721 A | 6/1999 | Nicholson et al. |
| 5,918,604 A | 7/1999 | Whelan |
| 5,919,193 A | 7/1999 | Slavitt |
| 5,919,194 A | 7/1999 | Anderson |
| 5,919,208 A | 7/1999 | Valenti |
| 5,919,215 A | 7/1999 | Wiklund et al. |
| 5,921,986 A | 7/1999 | Bonutti |
| 5,925,064 A | 7/1999 | Meyers et al. |
| 5,928,244 A | 7/1999 | Tovey et al. |
| 5,928,267 A | 7/1999 | Bonutti et al. |
| 5,931,838 A | 8/1999 | Vito |
| 5,931,869 A | 8/1999 | Boucher et al. |
| 5,940,942 A | 8/1999 | Fong |
| 5,941,900 A | 8/1999 | Bonutti |
| 5,941,901 A | 8/1999 | Egan |
| 5,944,750 A | 8/1999 | Tanner |
| 5,947,982 A | 9/1999 | Duran |
| 5,948,000 A | 9/1999 | Larsen et al. |
| 5,948,001 A | 9/1999 | Larsen |
| 5,948,002 A | 9/1999 | Bonutti |
| 5,951,590 A | 9/1999 | Goldfarb |
| 5,957,953 A | 9/1999 | DiPoto et al. |
| 5,961,499 A | 10/1999 | Bonutti et al. |
| 5,961,521 A | 10/1999 | Roger |
| 5,961,554 A | 10/1999 | Janson et al. |
| 5,964,765 A | 10/1999 | Fenton, Jr. et al. |
| 5,964,769 A | 10/1999 | Wagner et al. |
| 5,968,046 A | 10/1999 | Castleman |
| 5,968,047 A | 10/1999 | Reed |
| 5,980,520 A | 11/1999 | Vancaillie |
| 5,980,559 A | 11/1999 | Bonutti |
| 5,984,929 A | 11/1999 | Bashiri et al. |
| 5,989,282 A | 11/1999 | Bonutti |
| 5,993,458 A | 11/1999 | Vaitekunas et al. |
| 5,993,477 A | 11/1999 | Vaitekunas et al. |
| 6,007,567 A | 12/1999 | Bonutti |
| 6,007,580 A | 12/1999 | Lehto et al. |
| 6,010,525 A | 1/2000 | Bonutti et al. |
| 6,010,526 A | 1/2000 | Sandstrom et al. |
| 6,017,321 A | 1/2000 | Boone |
| 6,033,429 A | 3/2000 | Magovern |
| 6,033,430 A | 3/2000 | Bonutti |
| 6,045,551 A | 4/2000 | Bonutti |
| 6,050,998 A | 4/2000 | Fletcher |
| 6,056,751 A | 5/2000 | Fenton, Jr. |
| 6,056,772 A | 5/2000 | Bonutti |
| 6,056,773 A | 5/2000 | Bonutti |
| 6,059,797 A | 5/2000 | Mears |
| 6,059,817 A | 5/2000 | Bonutti et al. |
| 6,059,827 A | 5/2000 | Fenton, Jr. |
| 6,063,095 A | 5/2000 | Wang et al. |
| 6,066,151 A | 5/2000 | Miyawaki et al. |
| 6,066,160 A | 5/2000 | Colvin et al. |
| 6,066,166 A | 5/2000 | Bischoff et al. |
| 6,068,637 A | 5/2000 | Popov et al. |
| 6,068,648 A | 5/2000 | Cole |
| 6,077,277 A | 6/2000 | Mollenauer et al. |
| 6,077,292 A | 6/2000 | Bonutti |
| 6,080,161 A | 6/2000 | Eaves |
| 6,080,192 A | 6/2000 | Demopulos et al. |
| 6,083,243 A | 7/2000 | Pokropinski |
| 6,083,522 A | 7/2000 | Chu et al. |
| 6,086,593 A | 7/2000 | Bonutti |
| 6,086,608 A | 7/2000 | Ek et al. |
| 6,090,072 A | 7/2000 | Kratoska et al. |
| 6,099,531 A | 8/2000 | Bonutti |
| 6,099,537 A | 8/2000 | Sugai et al. |
| 6,099,550 A | 8/2000 | Yoon |
| 6,099,552 A | 8/2000 | Adams |
| 6,102,850 A | 8/2000 | Wang et al. |
| 6,106,545 A | 8/2000 | Egan |
| 6,117,160 A | 9/2000 | Bonutti |
| 6,120,536 A | 9/2000 | Ding et al. |
| 6,125,574 A | 10/2000 | Ganaja et al. |
| 6,126,677 A | 10/2000 | Ganaja et al. |
| 6,139,320 A | 10/2000 | Hahn |
| RE36,974 E | 11/2000 | Bonutti |
| 6,149,669 A | 11/2000 | Li |
| 6,152,949 A | 11/2000 | Bonutti |
| 6,155,756 A | 12/2000 | Mericle et al. |
| 6,159,224 A | 12/2000 | Yoon |
| 6,159,234 A | 12/2000 | Bonutti et al. |
| 6,171,299 B1 | 1/2001 | Bonutti |
| 6,171,307 B1 | 1/2001 | Orlich |
| 6,174,324 B1 | 1/2001 | Egan et al. |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer et al. |
| 6,190,401 B1 | 2/2001 | Green et al. |
| 6,200,322 B1 | 3/2001 | Branch et al. |
| 6,217,591 B1 | 4/2001 | Egan et al. |
| 6,224,593 B1 | 5/2001 | Ryan et al. |
| 6,224,630 B1 | 5/2001 | Bao et al. |
| 6,228,086 B1 | 5/2001 | Wahl et al. |
| 6,231,592 B1 | 5/2001 | Bonutti et al. |
| 6,238,395 B1 | 5/2001 | Bonutti |
| 6,238,396 B1 | 5/2001 | Bonutti |
| 6,258,091 B1 | 7/2001 | Sevrain et al. |
| 6,264,675 B1 | 7/2001 | Brotz |
| 6,267,761 B1 | 7/2001 | Ryan |
| 6,273,717 B1 | 8/2001 | Hahn et al. |
| 6,280,474 B1 | 8/2001 | Cassidy et al. |
| 6,286,746 B1 | 9/2001 | Egan et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,338,730 B1 | 1/2002 | Bonutti et al. |
| 6,340,365 B2 | 1/2002 | Dittrich et al. |
| 6,348,056 B1 | 2/2002 | Bates et al. |
| 6,358,271 B1 | 3/2002 | Egan et al. |
| 6,364,897 B1 | 4/2002 | Bonutti |
| 6,368,325 B1 | 4/2002 | McKinley et al. |
| 6,368,343 B1 | 4/2002 | Bonutti et al. |
| 6,371,957 B1 | 4/2002 | Amrein et al. |
| 6,409,742 B1 | 6/2002 | Fulton, III et al. |
| 6,409,743 B1 | 6/2002 | Fenton, Jr. |
| 6,419,704 B1 | 7/2002 | Ferree |
| 6,423,088 B1 | 7/2002 | Fenton, Jr. |

(56) References Cited

U.S. PATENT DOCUMENTS

| | | |
|---|---|---|
| 6,425,919 B1 | 7/2002 | Lambrecht |
| 6,428,562 B2 | 8/2002 | Bonutti |
| 6,432,115 B1 | 8/2002 | Mollenauer et al. |
| 6,447,516 B1 | 9/2002 | Bonutti |
| 6,450,985 B1 | 9/2002 | Schoelling et al. |
| 6,461,360 B1 | 10/2002 | Adam |
| 6,468,293 B2 | 10/2002 | Bonutti et al. |
| 6,475,230 B1 | 11/2002 | Bonutti et al. |
| 6,488,196 B1 | 12/2002 | Fenton, Jr. |
| 6,500,195 B2 | 12/2002 | Bonutti |
| 6,503,259 B2 | 1/2003 | Huxel et al. |
| 6,527,774 B2 | 3/2003 | Lieberman |
| 6,530,933 B1 | 3/2003 | Yeung et al. |
| 6,535,764 B2 | 3/2003 | Imran et al. |
| 6,544,267 B1 | 4/2003 | Cole et al. |
| 6,545,390 B1 | 4/2003 | Hahn et al. |
| 6,547,792 B1 | 4/2003 | Tsuji et al. |
| 6,551,304 B1 | 4/2003 | Whalen et al. |
| 6,554,852 B1 | 4/2003 | Oberlander |
| 6,557,426 B2 | 5/2003 | Reinemann, Jr. et al. |
| 6,558,390 B2 | 5/2003 | Cragg |
| 6,568,313 B2 | 5/2003 | Fukui et al. |
| 6,569,187 B1 | 5/2003 | Bonutti et al. |
| 6,572,635 B1 | 6/2003 | Bonutti |
| D477,776 S | 7/2003 | Pontaoe |
| 6,585,750 B2 | 7/2003 | Bonutti et al. |
| 6,585,764 B2 | 7/2003 | Wright et al. |
| 6,592,609 B1 | 7/2003 | Bonutti |
| 6,594,517 B1 | 7/2003 | Nevo |
| 6,605,090 B1 | 8/2003 | Trieu et al. |
| 6,610,080 B2 | 8/2003 | Morgan |
| 6,618,910 B1 | 9/2003 | Pontaoe |
| 6,623,486 B1 | 9/2003 | Weaver et al. |
| 6,623,487 B1 | 9/2003 | Goshert |
| 6,626,944 B1 | 9/2003 | Taylor |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer et al. |
| 6,645,227 B2 | 11/2003 | Fallin et al. |
| 6,652,585 B2 | 11/2003 | Lange |
| 6,666,877 B2 | 12/2003 | Morgan et al. |
| 6,669,705 B2 | 12/2003 | Westhaver et al. |
| 6,679,888 B2 | 1/2004 | Green et al. |
| 6,685,750 B1 | 2/2004 | Plos et al. |
| 6,699,240 B2 | 3/2004 | Francischelli |
| 6,702,821 B2 | 3/2004 | Bonutti |
| 6,705,179 B1 | 3/2004 | Mohtasham |
| 6,709,457 B1 | 3/2004 | Otte et al. |
| 6,719,765 B2 | 4/2004 | Bonutti |
| 6,719,795 B1 | 4/2004 | Cornwall |
| 6,719,797 B1 | 4/2004 | Ferree |
| 6,722,552 B2 | 4/2004 | Fenton, Jr. |
| 6,733,531 B1 | 5/2004 | Trieu |
| 6,764,513 B1 * | 7/2004 | Dowling .................. A61F 2/08 623/13.14 |
| 6,764,514 B1 | 7/2004 | Li et al. |
| 6,770,078 B2 | 8/2004 | Bonutti |
| 6,780,198 B1 | 8/2004 | Gregoire et al. |
| 6,786,989 B2 | 9/2004 | Torriani et al. |
| 6,796,003 B1 | 9/2004 | Marvel |
| 6,811,567 B2 | 11/2004 | Reiley |
| 6,818,010 B2 | 11/2004 | Eichhorn et al. |
| 6,823,871 B2 | 11/2004 | Schmieding |
| 6,830,589 B2 | 12/2004 | Erickson |
| 6,860,885 B2 | 3/2005 | Bonutti |
| 6,869,398 B2 | 3/2005 | Obenchain |
| 6,878,167 B2 | 4/2005 | Ferree |
| 6,890,334 B2 | 5/2005 | Brace et al. |
| 6,893,434 B2 | 5/2005 | Fenton et al. |
| 6,899,722 B2 | 5/2005 | Bonutti |
| 6,913,666 B1 | 7/2005 | Aeschlimann et al. |
| 6,916,321 B2 | 7/2005 | TenHuisen et al. |
| 6,921,264 B2 | 7/2005 | Mayer et al. |
| 6,923,824 B2 | 8/2005 | Morgan et al. |
| 6,932,835 B2 | 8/2005 | Bonutti et al. |
| 6,942,684 B2 | 9/2005 | Bonutti |
| 6,944,111 B2 | 9/2005 | Nakamura et al. |
| 6,955,540 B2 | 10/2005 | Mayer et al. |
| 6,955,683 B2 | 10/2005 | Bonutti |
| 6,958,077 B2 | 10/2005 | Suddaby |
| 6,981,983 B1 | 1/2006 | Rosenblatt et al. |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer et al. |
| 7,018,380 B2 | 3/2006 | Cole |
| 7,033,379 B2 | 4/2006 | Peterson |
| 7,048,755 B2 | 5/2006 | Bonutti et al. |
| 7,066,960 B1 | 6/2006 | Dickman |
| 7,087,073 B2 | 8/2006 | Bonutti |
| 7,090,111 B2 | 8/2006 | Egan et al. |
| 7,094,251 B2 | 8/2006 | Bonutti et al. |
| 7,104,996 B2 | 9/2006 | Bonutti |
| 7,128,763 B1 | 10/2006 | Blatt |
| 7,147,652 B2 | 12/2006 | Bonutti et al. |
| 7,160,405 B2 | 1/2007 | Aeschlimann et al. |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,241,297 B2 | 7/2007 | Shaolian et al. |
| 7,250,051 B2 | 7/2007 | Francischelli |
| 7,252,685 B2 | 8/2007 | Bindseil et al. |
| 7,273,497 B2 | 9/2007 | Ferree |
| 7,326,200 B2 | 2/2008 | Trieu |
| 7,329,263 B2 | 2/2008 | Bonutti et al. |
| 7,335,205 B2 | 2/2008 | Aeschlimann et al. |
| 7,377,930 B2 | 5/2008 | Loughran |
| 7,429,266 B2 | 9/2008 | Bonutti et al. |
| 7,445,634 B2 | 11/2008 | Trieu |
| 7,481,825 B2 | 1/2009 | Bonutti |
| 7,481,831 B2 | 1/2009 | Bonutti |
| 7,510,895 B2 | 3/2009 | Raterman |
| 7,854,750 B2 | 12/2010 | Bonutti et al. |
| 7,879,072 B2 | 2/2011 | Bonutti et al. |
| 7,891,691 B2 | 2/2011 | Bearey |
| 7,967,820 B2 | 6/2011 | Bonutti et al. |
| 8,128,669 B2 | 3/2012 | Bonutti |
| 8,140,982 B2 | 3/2012 | Hamilton, II et al. |
| 8,147,514 B2 | 4/2012 | Bonutti |
| 8,162,977 B2 | 4/2012 | Bonutti et al. |
| 2001/0002440 A1 | 5/2001 | Bonutti |
| 2001/0009250 A1 | 7/2001 | Herman et al. |
| 2001/0041916 A1 | 11/2001 | Bonutti |
| 2002/0016593 A1 | 2/2002 | Hearn et al. |
| 2002/0016633 A1 | 2/2002 | Lin et al. |
| 2002/0019649 A1 | 2/2002 | Sikora et al. |
| 2002/0026244 A1 | 2/2002 | Trieu |
| 2002/0029083 A1 | 3/2002 | Zucherman et al. |
| 2002/0029084 A1 | 3/2002 | Paul et al. |
| 2002/0045902 A1 | 4/2002 | Bonutti |
| 2002/0062153 A1 | 5/2002 | Paul et al. |
| 2002/0103495 A1 | 8/2002 | Cole |
| 2002/0120269 A1 | 8/2002 | Lange |
| 2002/0120270 A1 * | 8/2002 | Trieu .................. A61B 17/7022 623/13.11 |
| 2002/0120281 A1 | 8/2002 | Overaker |
| 2002/0123750 A1 | 9/2002 | Eisermann et al. |
| 2002/0143329 A1 | 10/2002 | Serhan |
| 2002/0183762 A1 | 12/2002 | Anderson et al. |
| 2002/0188301 A1 | 12/2002 | Dallara et al. |
| 2003/0039196 A1 | 2/2003 | Nakamura et al. |
| 2003/0040758 A1 | 2/2003 | Wang et al. |
| 2003/0065361 A1 | 4/2003 | Dreyfuss |
| 2003/0105474 A1 | 6/2003 | Bonutti |
| 2003/0118518 A1 | 6/2003 | Hahn et al. |
| 2003/0130735 A1 | 7/2003 | Rogalski |
| 2003/0158582 A1 | 8/2003 | Bonutti et al. |
| 2003/0167072 A1 | 9/2003 | Oberlander |
| 2003/0181800 A1 | 9/2003 | Bonutti |
| 2003/0181889 A1 * | 9/2003 | Little .................. A61K 9/0024 604/891.1 |
| 2003/0195514 A1 | 10/2003 | Trieu et al. |

(56) References Cited

U.S. PATENT DOCUMENTS

| | | |
|---|---|---|
| 2003/0195530 A1 | 10/2003 | Thill |
| 2003/0195565 A1 | 10/2003 | Bonutti |
| 2003/0204204 A1 | 10/2003 | Bonutti |
| 2003/0208203 A1 | 11/2003 | Lim |
| 2003/0216742 A1 | 11/2003 | Wetzler |
| 2003/0225438 A1 | 12/2003 | Bonutti et al. |
| 2003/0229361 A1 | 12/2003 | Jackson |
| 2004/0010287 A1 | 1/2004 | Bonutti |
| 2004/0024457 A1* | 2/2004 | Boyce .................. A61F 2/08 623/13.17 |
| 2004/0024459 A1 | 2/2004 | Ferree |
| 2004/0030341 A1 | 2/2004 | Aeschlimann et al. |
| 2004/0034357 A1 | 2/2004 | Beane et al. |
| 2004/0039392 A1 | 2/2004 | Trieu |
| 2004/0059333 A1 | 3/2004 | Carl |
| 2004/0097939 A1 | 5/2004 | Bonutti |
| 2004/0098050 A1 | 5/2004 | Foerster et al. |
| 2004/0127907 A1 | 7/2004 | Dakin |
| 2004/0127989 A1 | 7/2004 | Dooris |
| 2004/0133077 A1 | 7/2004 | Obenchain |
| 2004/0138703 A1 | 7/2004 | Alleyne |
| 2004/0143334 A1 | 7/2004 | Ferree |
| 2004/0167548 A1 | 8/2004 | Bonutti |
| 2004/0186471 A1 | 9/2004 | Trieu |
| 2004/0215199 A1 | 10/2004 | Zinkel |
| 2004/0220616 A1 | 11/2004 | Bonutti et al. |
| 2004/0225325 A1 | 11/2004 | Bonutti |
| 2004/0230223 A1 | 11/2004 | Bonutti et al. |
| 2004/0236374 A1 | 11/2004 | Bonutti et al. |
| 2005/0033366 A1 | 2/2005 | Cole et al. |
| 2005/0033434 A1 | 2/2005 | Berry |
| 2005/0038514 A1 | 2/2005 | Helm et al. |
| 2005/0043733 A1 | 2/2005 | Eisermann |
| 2005/0043742 A1 | 2/2005 | Bruneau |
| 2005/0043796 A1 | 2/2005 | Grant et al. |
| 2005/0055096 A1 | 3/2005 | Serhan |
| 2005/0070765 A1 | 3/2005 | Abdelgany |
| 2005/0071012 A1 | 3/2005 | Serhan et al. |
| 2005/0075644 A1 | 4/2005 | DiPoto |
| 2005/0090827 A1 | 4/2005 | Gedebou |
| 2005/0096699 A1 | 5/2005 | Wixey et al. |
| 2005/0113928 A1 | 5/2005 | Cragg et al. |
| 2005/0125072 A1 | 6/2005 | Kolb |
| 2005/0126680 A1 | 6/2005 | Aeschlimann et al. |
| 2005/0143826 A1 | 6/2005 | Zucherman et al. |
| 2005/0149024 A1 | 7/2005 | Ferrante et al. |
| 2005/0149029 A1 | 7/2005 | Bonutti |
| 2005/0197537 A1 | 9/2005 | Bonadio |
| 2005/0203521 A1 | 9/2005 | Bonutti |
| 2005/0216059 A1 | 9/2005 | Bonutti et al. |
| 2005/0216087 A1 | 9/2005 | Zucherman et al. |
| 2005/0222620 A1 | 10/2005 | Bonutti |
| 2005/0234460 A1 | 10/2005 | Miller |
| 2005/0240190 A1 | 10/2005 | Gall et al. |
| 2005/0240227 A1 | 10/2005 | Bonutti |
| 2005/0246021 A1 | 11/2005 | Ringeisen et al. |
| 2005/0255140 A1* | 11/2005 | Hagan ................... A61F 2/0811 424/423 |
| 2005/0256582 A1 | 11/2005 | Ferree |
| 2005/0261684 A1 | 11/2005 | Shaolian et al. |
| 2005/0267481 A1 | 12/2005 | Carl et al. |
| 2005/0267534 A1 | 12/2005 | Bonutti et al. |
| 2005/0283246 A1 | 12/2005 | Cauthen |
| 2006/0009846 A1 | 1/2006 | Trieu et al. |
| 2006/0009855 A1 | 1/2006 | Goble et al. |
| 2006/0015101 A1 | 1/2006 | Warburton et al. |
| 2006/0015108 A1 | 1/2006 | Bonutti |
| 2006/0024357 A1 | 2/2006 | Carpenter et al. |
| 2006/0026244 A1 | 2/2006 | Watson |
| 2006/0064095 A1 | 3/2006 | Senn et al. |
| 2006/0089646 A1 | 4/2006 | Bonutti |
| 2006/0122600 A1 | 6/2006 | Cole |
| 2006/0122704 A1 | 6/2006 | Vresilovic et al. |
| 2006/0142799 A1 | 6/2006 | Bonutti |
| 2006/0167495 A1 | 7/2006 | Bonutti et al. |
| 2006/0200199 A1 | 9/2006 | Bonutti et al. |
| 2006/0212073 A1 | 9/2006 | Bonutti et al. |
| 2006/0217765 A1 | 9/2006 | Bonutti et al. |
| 2006/0229623 A1 | 10/2006 | Bonutti et al. |
| 2006/0235470 A1 | 10/2006 | Bonutti et al. |
| 2006/0241695 A1 | 10/2006 | Bonutti et al. |
| 2006/0264953 A1 | 11/2006 | Falahee |
| 2006/0265009 A1 | 11/2006 | Bonutti |
| 2006/0265011 A1 | 11/2006 | Bonutti |
| 2007/0032825 A1 | 2/2007 | Bonutti et al. |
| 2007/0088362 A1 | 4/2007 | Bonutti et al. |
| 2007/0118129 A1 | 5/2007 | Fraser et al. |
| 2007/0198555 A1 | 8/2007 | Friedman et al. |
| 2007/0233092 A1 | 10/2007 | Falahee |
| 2007/0265561 A1 | 11/2007 | Yeung |
| 2007/0270833 A1 | 11/2007 | Bonutti et al. |
| 2008/0021474 A1 | 1/2008 | Bonutti et al. |
| 2008/0039845 A1 | 2/2008 | Bonutti et al. |
| 2008/0039873 A1 | 2/2008 | Bonutti et al. |
| 2008/0046090 A1 | 2/2008 | Paul et al. |
| 2008/0097448 A1 | 4/2008 | Binder et al. |
| 2008/0108897 A1 | 5/2008 | Bonutti et al. |
| 2008/0108916 A1 | 5/2008 | Bonutti et al. |
| 2008/0114399 A1 | 5/2008 | Bonutti |
| 2008/0132950 A1 | 6/2008 | Lange |
| 2008/0140116 A1 | 6/2008 | Bonutti |
| 2008/0140117 A1 | 6/2008 | Bonutti et al. |
| 2008/0195145 A1 | 8/2008 | Bonutti et al. |
| 2008/0269753 A1 | 10/2008 | Cannestra |
| 2008/0269808 A1 | 10/2008 | Gall et al. |
| 2009/0024161 A1 | 1/2009 | Bonutti et al. |
| 2009/0093684 A1 | 4/2009 | Schorer |
| 2009/0138014 A1 | 5/2009 | Bonutti |
| 2009/0194969 A1 | 8/2009 | Bearey |
| 2010/0211120 A1 | 8/2010 | Bonutti et al. |
| 2011/0060375 A1 | 3/2011 | Bonutti |
| 2011/0295253 A1 | 12/2011 | Bonutti et al. |
| 2012/0165841 A1 | 6/2012 | Bonutti |
| 2012/0191140 A1 | 7/2012 | Bonutti |
| 2012/0215233 A1 | 8/2012 | Bonutti et al. |
| 2013/0030735 A1 | 1/2013 | Jau et al. |

FOREIGN PATENT DOCUMENTS

| | | |
|---|---|---|
| CA | 2698057 A1 | 3/2009 |
| DE | 1903316 U | 10/1964 |
| DE | 1903016 A1 | 8/1970 |
| DE | 3517204 A1 | 11/1986 |
| DE | 3722538 A1 | 1/1989 |
| DE | 9002844 U1 | 12/1990 |
| EP | 773004 A1 | 5/1997 |
| EP | 784454 A1 | 7/1997 |
| EP | 1614525 A1 | 1/2006 |
| EP | 1988837 A2 | 11/2008 |
| EP | 2134294 A2 | 12/2009 |
| FR | 2696338 A1 | 4/1994 |
| FR | 2717368 A1 | 9/1995 |
| FR | 2728779 A1 | 7/1996 |
| FR | 2736257 A1 | 1/1997 |
| FR | 2750031 A1 | 12/1997 |
| FR | 2771621 A1 | 6/1999 |
| FR | 2785171 A1 | 5/2000 |
| GB | 2093701 A | 9/1982 |
| GB | 2306110 A | 4/1997 |
| JP | H08-140982 A | 6/1996 |
| SU | 184396 | 10/1964 |
| WO | 9112779 A1 | 9/1991 |
| WO | 9323094 A1 | 11/1993 |
| WO | 9408642 A1 | 4/1994 |
| WO | 9516398 A1 | 6/1995 |
| WO | 9531941 A1 | 11/1995 |
| WO | 9614802 A1 | 5/1996 |
| WO | 9712779 A1 | 4/1997 |
| WO | 9749347 A1 | 12/1997 |
| WO | 9811838 A1 | 3/1998 |
| WO | 9826720 A1 | 6/1998 |
| WO | 2002053011 A2 | 7/2002 |
| WO | 2007092869 A2 | 8/2007 |
| WO | 2008116203 A2 | 9/2008 |

(56) References Cited

FOREIGN PATENT DOCUMENTS

| WO | 2009029908 A1 | 3/2009 |
|---|---|---|
| WO | 2009124215 A1 | 10/2009 |
| WO | 2010099222 A1 | 9/2010 |

OTHER PUBLICATIONS

Office Action dated Mar. 19, 2015 in U.S. Appl. No. 14/032,969 by Bonutti.
Office Action dated Jun. 11, 2015 in U.S. Appl. No. 14/076,812 by Bonutti.
Office Action dated Jun. 8, 2016 in U.S. Appl. No. 14/076,818, by Bonutti.
Office Action dated Jun. 21, 2016 in U.S. Appl. No. 14/204,522, by Bonutti.
Office Action dated Jun. 14, 2016 in U.S. Appl. No. 14/205,592, by Bonutti.
IPR—International Publication W02009/029908, published 05/0312009 for PCT/US08/74941.
ISR—International Search Report, W02009/029908, published May 3, 2009 for PCT/US08/74941.
IPER—Internation Preliminary Report on Patentability, W02009/029908, published Mar. 2, 2010 for PCT/US08/74941.
Written Opinion W02009/029908 dated Feb. 28, 2010 for PCT/US08/74941.
International Search Report PCT/US2010/025263 completed Apr. 13, 2010.
Written Opinion for PCT/US2010/025263 completed Apr. 13, 2010.
European Search Report dated Sep. 10, 2012 for EP08732724.3 (046).
Office Action dated Nov. 8, 2013 in U.S. Appl. No. 11/258,795 by Bonutti.
010-3 Copending U.S. Appl. No. 11/932,907—RCE Response dated Sep. 15, 2011.
027 Copending U.S. Appl. No. 11/258,795 Non-Final Office Action dated Apr. 26, 2011
046 Copending U.S. Appl. No. 11/689,670, RCE Response dated Sep. 19, 2011
003-1 Copending U.S. Appl. No. 10/614,352, Final Office Action dated Jul. 12, 2010.
007-2 Copending U.S. Appl. No. 11/932,602 Final Response to Office Action dated Jun. 10, 2011.
039 Copending U.S. Appl. No. 11/671,556, Response filed Aug. 23, 2010
Co-pending U.S. Appl. No. 11/438,537, Supplemental Final Rejection dated Sep. 25, 2009.
Petition for Inter Partes Review of U.S. Pat. No. 5,980,559, IPR 2013-00603, Filing Date Sep. 24, 2013.
Declaration of David Kaplan, PHD. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 26, 2013, Sept 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, P 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , J. of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et ai, Repair of the Tibiofibular Syndesmosis with a Flexible Implant, J. of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.
Office Action dated Aug. 20, 2013 in U.S. Appl. No. 12/576,992 by Bonutti.
Int'l Search Report and Written Opinion dated Dec. 1, 2010 in Int'l Application No. PCT/US2010/052018.
Office Action dated Jan. 29, 2014 in U.S. Appl. No. 14/032,969.
Office Action dated Mar. 13, 2014 in U.S. Appl. No. 14/076,812 by Bonutti.
The Search for the Holy Grail: A Century of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1 014984.066, Ultrasonic Welding, (c) 1999.
Guide to Ultrasound Plastic Assembly, Ultrasonic Division Publication, (c) 1995.
Branson, Polymers: Characteristics and Compatibility for Ultrasonic Assembly, Applied Technologies Group, Publication unknown (admitted prior art).
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Corp., (c) 1992.
IPR—International Publication WO/2007/092869, published Aug. 16, 2007 for PCT/US2007/061730.

(56) References Cited

OTHER PUBLICATIONS

ISR—International Search Report WO/2007/092869, published Dec. 13, 2007 for PCT/US2007/061730.
Inti Prelim Report on Patentability, WO/2007/092869, published Aug. 12, 2008 for PCT/US2007/061730.
Written Opinion WO/2007/092869 dated Aug. 7, 2008 for PCT/US2007/061730.
Arthrex, Protect your graft, Am J Sports Med, vol. 22, No. 4, Jul.-Aug. 1994.
Barrett et ai, T-Fix endoscopic meniscal repair: technique and approach to different types of tears, Apr. 1995, Arthroscopy, vol. 11 No. 2 p. 245-251.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510K, Summary for Arthrex Inc.'s Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Sand. j. of Med & Science in Sports, 1995, 5:170-174.
Madjar et ai, Minimally Invasive Pervaginam Procedures, for the Treatment of Female Stress Incontinence . . . , Artificial Organs, 22 (10) 879-885,1998.
Nowak et ai, Comparative Study of Fixation Techniques in the Open Bankart Operation Using Either a Cannulated Screw or Suture-Anchors, Acta Orthopcedica Belgica, vol. 64-2—1998.
Packer et ai, Repair of Acute Scapho-Lunate Dissociation Facilitated by the "TAG"* Suture Anchor, Journal of Hand Surgery (British and European Volume, 1994) 19B: 5: 563-564.
Richmond, Modificatio of the Bankart reconstruction with a suture anchor, Am J Sports Med, vol. 19, No. 4, p. 343-346, 1991.
Shea et ai, Technical Note: Arthroscopic Rotator Cuff Repair Using a Transhumeral Approach to Fixation, Arthroscopy: The Journal of Arthroscopic and Related Surgery, vol. 14, No. 1 Jan.-Feb. 1998: pp. 118-122.
Tfix, Acufex just tied the knot . . . , Am. J. Sports Med., vol. 22, No. 3, May-Jun. 1994.
Wong et ai, Case Report: Proper Insertion Angle is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 Feb. 2010: pp. 286-290.
Cobb et ai, Late Correction of Malunited Intercondylar Humeral Fractures Intra-Articular Osteotomy and Tricortical Bone Grafting, J BoneJointSurg [Br] 1994; 76-B:622-6.
Fellinger, et ai, Radial avulsion of the triangular fibrocartilage complex in acute wrist trauma: a new technique for arthroscopic repair, Jun. 1997, Arthroscopy vol. 13 No. 3 p. 370-374.
Hecker et al , Pull-out strength of suture anchors for rotator cuff and Bankart lesion repairs, Nov.-Dec. 1993, The American Journal of Sports Medicine, vol. 21 No. 6 p. 874-879.
Hernigou et al, Proximal Tibial Osteotomy for Osteoarthritis with Varus Deformity a Ten to Thirteen-Year Follow-Up Study, J Bone Joint Surg, vol. 69-A, No. 3. March 1987, p. 332-354.
Ibarra et al, "Glenoid Replacement in Total Shoulder Arthroplastly," The Orthopedic Clinics of North America—Total Shoulder Arthroplasty, vol. 29, No. 3, pp. 403-413 (Jul. 1998).

Mosca et al, "Calcaneal Lengthening for Valgus Deformity of the Hindfoot," The Journal of Bone and Joint Surgery, vol. 77-A, No. 4, pp. 500-512 (Apr. 1995).
Murphy et al, "Radial Opening Wedge Osteotomy in Madelung's Deformity," The Journal of Hand Surgery, vol. 21A, No. 6, pp. 1035-1044 (Nov. 1996).
Biomet, Stanmore Modular Hip, J. Bone Joint Surg., vol. 76-B : No. Two, Mar. 1994.
Inti Prelim Rep on Patentability and Written Opinion for PCT/US10/25263 dated Aug. 30, 2011.
IPR—International Publication W0/200S/116203, published Sep. 22, 2009 for PCT/USOS/5794S.
ISR—International Search Report W0/200S/116203, published Dec. 24, 2008 for PCT/USOS/5794S.
IPER—Internation Preliminary Report on Patentability, WO/2008/116203, published Sep. 22, 2009 for PCT/US08/57948.
Written Opinion WO/2008/116203 dated Oct. 23, 2008 for PCT/USO8/57948.
Office Action dated Nov. 10, 2014 in U.S. Appl. No. 14/076,812 by Bonutti.
Final Office Action dated Dec. 2, 2016 relating to U.S. Appl. No. 11/258,795, 16 pages.
Non-Final Office Action dated May 11, 2016 relating to U.S. Appl. No. 11/258,795, 15 pages.
Final Office Action dated Aug. 10, 2015 relating to U.S. Appl. No. 11/258,795, 14 pages.
Non-Final Office Action dated Mar. 27, 2015 relating to U.S. Appl. No. 11/258,795, 13 pages.
Final Office Action dated May 16, 2014 relating to U.S. Appl. No. 11/258,795, 13 pages.
Non-Final Office Action dated Nov. 8, 2013 relating to U.S. Appl. No. 11/258,795, 15 pages.
Final Office Action dated Dec. 20, 2011 relating to U.S. Appl. No. 11/258,795, 12 pages.
Non-Final Office Action dated Apr. 26, 2011 relating to U.S. Appl. No. 11/258,795, 12 pages.
Final Office Action dated Mar. 2, 2010 relating to U.S. Appl. No. 11/258,795, 11 pages.
Non-Final Office Action dated Sep. 19, 2008 relating to U.S. Appl. No. 11/258,795, 6 pages.
Non-Final Office Action dated Nov. 24, 2015 relating to U.S. Appl. No. 11/576,992, 21 pages.
Final Office Action dated Feb. 4, 2015 relating to U.S. Appl. No. 12/576,992, 21 pages.
Non-Final Office Action dated Sep. 4, 2014 relating to U.S. Appl. No. 12/576,992, 20 pages.
Final Office Action dated Jan. 17, 2014 relating to U.S. Appl. No. 12/576,992, 21 pages.
Non-Final Office Action dated Aug. 20, 2013 relating to U.S. Appl. No. 12/576,992, 24 pages.
Non-Final Office Action dated Mar. 1, 2017 relating to U.S. Appl. No. 12/872,140, 9 pages.
Final Office Action dated Jun. 30, 2016 relating to U.S. Appl. No. 12/872,140, 5 pages.
Non-Final Office Action dated Nov. 25, 2015 relating to U.S. Appl. No. 12/872,140, 8 pages.
Final Office Action dated Mar. 3, 2015 relating to U.S. Appl. No. 12/872,140, 6 pages.
Non-Final Office Action dated Jun. 9, 2014 relating to U.S. Appl. No. 12/872,140, 12 pages.
Final Office Action dated Nov. 6, 2012 relating to U.S. Appl. No. 12/872,140, 9 pages.
Non-Final Office Action dated Apr. 19, 2012 relating to U.S. Appl. No. 12/872,140, 12 pages.
Non-Final Office Action dated Feb. 11, 2015 relating to U.S. Appl. No. 13/873,389, 12 pages.
Final Office Action dated Jul. 31, 2015 relating to U.S. Appl. No. 13/873,389, 13 pages.
Non-Final Office Action dated Feb. 17, 2016 relating to U.S. Appl. No. 13/873,389, 13 pages.
Final Office Action dated Sep. 1, 2016 relating to U.S. Appl. No. 13/873,389, 15 pages.

(56) References Cited

OTHER PUBLICATIONS

Non-Final Office Action dated Mar. 19, 2015 relating to U.S. Appl. No. 14/032,969, 14 pages.
Final Office Action dated Jun. 27, 2014 relating to U.S. Appl. No. 14/032,969, 14 pages.
Non-Final Office Action dated Jan. 29, 2014 relating to U.S. Appl. No. 14/032,969, 11 pages.
Non-Final Office Action dated Jun. 11, 2015 relating to U.S. Appl. No. 14/076,812, 12 pages.
Final Office Action dated Nov. 10, 2014 relating to U.S. Appl. No. 14/076,812, 13 pages.
Non-Final Office Action dated Mar. 13, 2014 relating to U.S. Appl. No. 14/076,812, 10 pages.
Non-Final Office Action dated Jun. 8, 2016 relating to U.S. Appl. No. 14/076,818, 11 pages.
Final Office Action dated Nov. 21, 2016 relating to U.S. Appl. No. 14/076,818, 12 pages.
Non-Final Office Action dated Jun. 14, 2016 relating to U.S. Appl. No. 14/205,592, 7 pages.
Non-Final Office Action dated Jun. 21, 2016 relating to U.S. Appl. No. 14/204,522, 12 pages.
Non-Final Office Action dated Jun. 26, 2017 relating to U.S. Appl. No. 13/873,389, 14 pages.
Non-Final Office Action dated Jul. 3, 2017 relating to U.S. Appl. No. 11/258,795, 16 pages.
Final Office Action dated Jul. 6, 2017 relating to U.S. Appl. No. 12/872,140, 11 pages.

\* cited by examiner

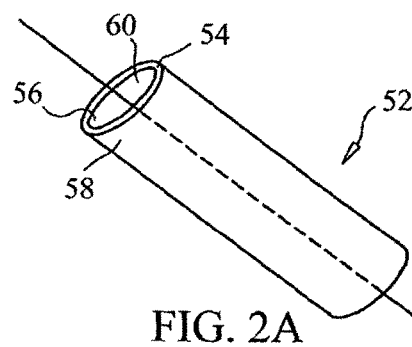
FIG. 2A
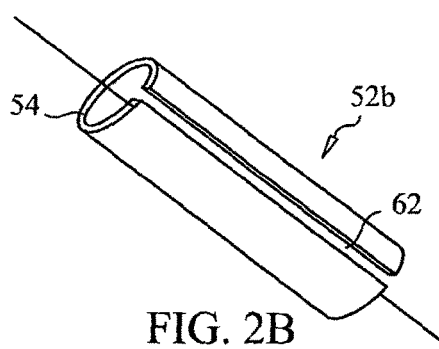
FIG. 2B
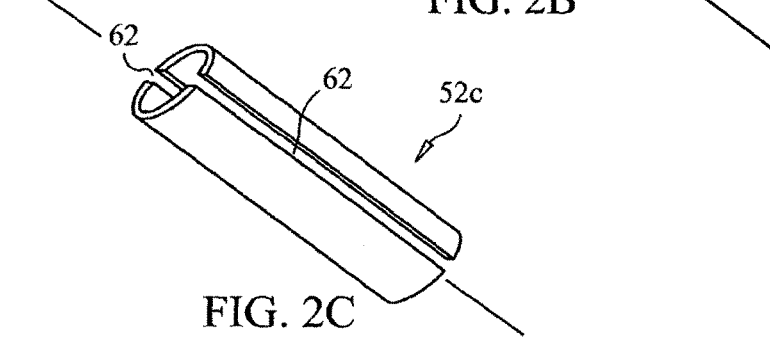
FIG. 2C
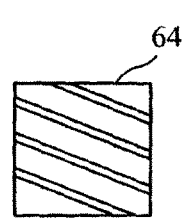 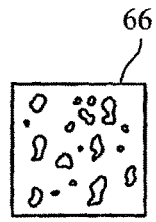 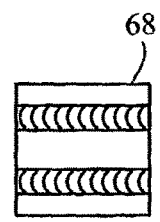 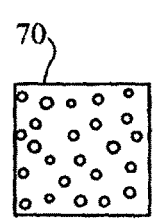
FIG. 2D   FIG. 2E   FIG. 2F   FIG. 2G

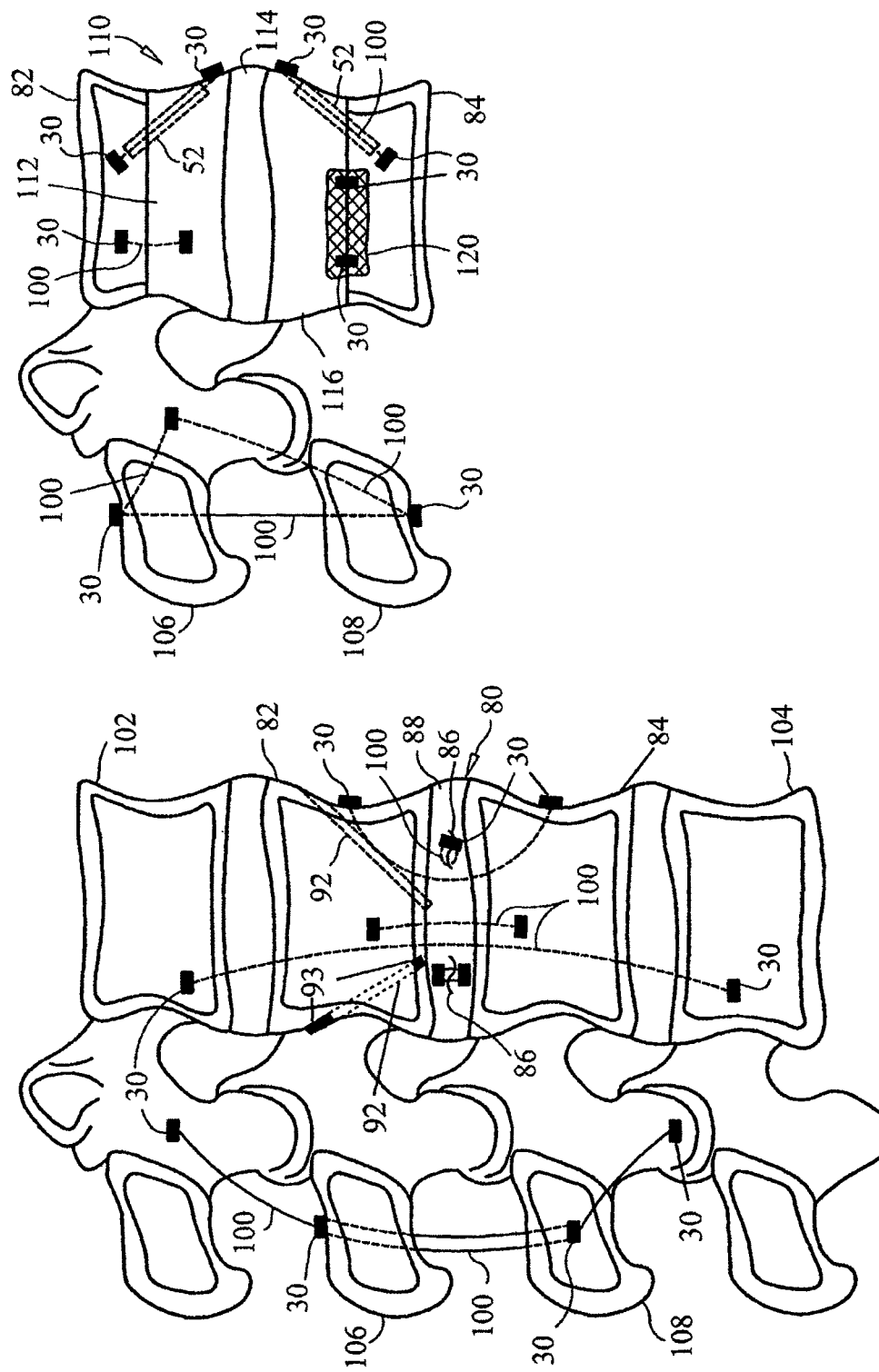

DEVICES AND METHODS FOR STABILIZING TISSUE AND IMPLANTS

CROSS-REFERENCE TO RELATED APPLICATION

This application is a continuation of U.S. patent application Ser. No. 11/258,795, filed Oct. 26, 2005, which claims the benefit of U.S. Provisional Patent Application No. 60/622,095, filed Oct. 26, 2004, the entirety of which is incorporated herein by reference.

FIELD OF THE INVENTION

The present invention generally relates to devices and methods for repairing and stabilizing tissue and implants. Specifically, the present invention provides devices and methods for repairing, reconstructing, augmenting, and stabilizing joints of the body, and more particularly, the knee and joints of the spine (including intervertebral discs and adjacent bones).

BACKGROUND OF THE INVENTION

During a surgical procedure, tissue is either intentionally or accidentally displaced, torn, or fractured to create a pathway to a desired operation site. In doing so, this tissue is damaged to a point where it may not function properly. After the intended surgical procedure or implantation is performed at the operation site, the skin incision is approximated. Currently, however, the other tissue like the muscles, ligaments, tendons, cartilage, bones, etc. which were damaged to create the pathway are not necessarily repaired or reconstructed. For example, following spinal surgery, a frequent complication is late instability where there is shearing antero-posteriorly or superior inferiorly due to excess motion because the ligaments have been damaged during surgical exposure. This complication may lead to degenerative disc disease and lower back pain.

Various methods and devices have been disclosed for repairing tissue. For example, U.S. Pat. No. 6,425,919 issued to Lambrecht discloses a disc herniation constraining device for implantation into the disc. The constraining device includes a fastener, a barrier, and a support member connecting the fastener and barrier. The barrier closes a defect in the annulus of the disc, while the fastener supports the position of the barrier. The barrier is placed between the annulus and the nucleus of the disc. The barrier may include a sealant and an enlarger.

In another example, U.S. Pat. No. 6,592,625 issued to Cauthen discloses a collapsible patch which is inserted through a surgical incision or rupture of the annulus. The patch is positioned within the subannular space. The patch expands to bridge the incision or rupture thereby occluding the aperture from the interior of the disc and preventing migration of nucleus pulposus.

U.S. Pat. No. 6,679,889 issued to West, Jr. et al discloses a method and apparatus of repairing the anterior cruciate ligament. The device enables the surgeon to independently apply a desired tensile load onto individual strands of a multiple-stranded soft tissue graft. The device is equipped with structure for fastening or otherwise attaching the device to a patient's limb during the conditioning and pre-tensioning procedure.

Additionally, U.S. Pat. No. 6,699,286 issued to Sklar discloses methods and apparatus of making repairs with graft ligaments. The method for graft ligament reconstruction includes harvesting a graft ligament consisting entirely of soft tissue. The graft ligament is compacted through compression so as to significantly reduce the cross-sectional area and increase the density of the collagen material of the graft ligament. The compressed graft ligament is deployed within the human body.

Various methods and devices have been disclosed for inserting an implant within the body. For example, U.S. Pat. No. 5,108,438 issued to Stone discloses a mesh skirt to anchor a prosthetic intervertebral disc. The implant includes a dry, porous, volume matrix of biocompatible and bioabsorbable fibers which may be interspersed with glyscosaminoglycan molecules. The matrix is adapted to have an outer surface contour substantially the same as that of a natural intervertebral disc. A mesh member extends from the lateral surface of the implant. After implantation, the mesh member may be sutured to adjacent tissue to anchor the disc in place. The mesh member may function in this capacity until sufficient tissue ingrowth occurs to provide that function.

In another example, U.S. Pat. No. 6,733,531 issued to Trieu discloses a spinal implant which is anchored using a device having an elongated anchoring body, such as an anchoring rod, and at least one securing member attached to the anchoring rod. The anchoring body or rod is configured to anchor, hold, or otherwise retain a spinal implant. The securing members are spaced apart along the length of the anchoring rod and may define a region for disposing an implant therebetween. The anchoring rod has a first end and a second end, wherein the first end is securable to an adjacent vertebra.

Once tissue has been repaired or an implant has been inserted within the body, the repaired region and surrounding tissue may be stabilized to enhance healing. U.S. Pat. No. 6,652,585 issued to Lange discloses a spine stabilization system including a flexible member attachable to a portion of the spinal column. The member includes components that are oriented and function similar to the natural fiber orientation of the anterior longitudinal ligament and annulus tissue. The use of components resist loading applied by extension and rotation of the spine, while the flexibility of the member does not subject it to the compressive loading of the spinal column segment to which it is attached.

In addition, U.S. Pat. No. 6,293,949 issued to Justis et al. discloses a device for stabilizing the spinal column. The device includes a longitudinal member sized to span a distance between at least two vertebral bodies and being at least partially formed of a shape-memory material exhibiting pseudoelastic characteristics at about human body temperature. The longitudinal member is reformed from an initial configuration to a different configuration in response to the imposition of stress caused by relative displacement between the vertebral bodies, and recovers toward the initial configuration when the stress is removed to thereby provide flexible stabilization to the spinal column.

There exists a need for devices and methods for repairing, reconstructing, augmenting, and securing tissue or an implant during surgery and "on the way out" after surgery has been performed at an intended operation site. Upon completion of the intended surgery, tissue may be compressed to other tissue or an implant to improve healing. Hard tissue, for example, may require rigid fixation while soft tissue to require flexible fixation. The repair, reconstruction, and augmentation of tissue and the securing of implants "on the way out" of the body after performing a surgical procedure creates a stabilized and enhanced healing environment

SUMMARY OF THE INVENTION

The present invention provides for the repair, reconstruction, augmentation, and securing of tissue or implants during a surgical procedure and "on the way out" after the surgical procedure has been performed. Hard and soft tissue at and around the operation site and tissue between the operation site and the skin incision may be compressed and/or rebuilt so that tissue-function may be at least partially restored and the operation region may be stabilized for enhanced healing. This could be ligament repair, tendon repair, muscle repair, bone repair, cartilage repair, and repair of any other tissue type. Ligaments may be fastened to ligaments; ligaments to bones; bones to bones; ligaments to muscles; muscles to muscles; tissue grafts to bone; tissue grafts to ligaments; grafts to grafts; and any other combination of tissue and implants. It is further contemplated that the methods and devices of the present invention may be utilized with minimally invasive techniques.

In accordance with one aspect of the present invention, a method for stabilizing a body joint is provided. A fastener is positioned in contact with first body tissue on one side of the joint. Another fastener is positioned in contact with second body tissue on the other side of the joint. A suture is placed between the fasteners and tensioned. The tensioned suture is secured to the fasteners to restrict normal movement of the joint. The fasteners may be positioned in contact with the outer surface of the body tissues or inside of the body tissues. The suture may be positioned adjacent to the joint, through the joint, or in combination.

The body tissues may be bones, muscles, ligaments, tendons, nerves, skin, organs, cartilage, fascia, and blood vessels. The bones and ligaments may be bones and ligaments of the knee, ankle, elbow, wrist, feet, hand, hip, shoulder, jaw, and spine. Specifically, bones of the knee may include the femur, tibia, and patella. Ligaments of the knee may include the medial collateral ligament, lateral collateral ligament, posterior oblique ligament, arcuate ligament, oblique popliteal ligament, anterior cruciate ligament, and posterior cruciate ligament. Bones of the spine may include transverse process, pedicle, facet, spinous process, posterior arch, odontoid process, posterior tubercle, lateral articular process, uncinate process, anterior tubercle, carotid tubercle, odontoid process, lamina, and vertebral body. Ligaments of the spine may include the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine.

A tubular member may be positioned between the fasteners, and the suture may be placed within the tubular member such that a portion of the tubular member contacts the first body part and another portion of the tubular member contacts the second body part thereby maintaining the body parts in alignment with each other.

In accordance with another aspect of the present invention, there is provided a method for approximating an incision in tissue. A suture is positioned in portions of tissue located on opposite sides of the incision. The proximal and distal ends of the suture extend from the tissue and are adjacent the incision. A fastener is placed transverse to the incision with the ends of the suture disposed within at least one channel of the fastener. The suture is tensioned and secured to the fastener to thereby approximate the incision. The tissue may be bone, muscle, ligament, tendon, skin, organ, cartilage, and blood vessels.

Additionally, two fasteners may be positioned generally parallel to an incision with the first fastener placed on one side of the incision and the second fastener placed on the opposite side of the incision. A suture may be positioned in portions of tissue located on opposite sides of the incision with the middle section of the suture slidably disposed within at least one channel of the first fastener and the end portions of the suture disposed within at least one channel of the second fastener. The suture may be tensioned and secured to the fasteners to thereby approximate the incision.

In accordance with another aspect of the present invention, a fastener is provided. The fastener includes an elongated member and at least one channel extending therethrough generally perpendicular to the longitudinal axis of the elongated member. A portion of the outer surface of the fastener may be concave, flat, and/or convex.

There is also provided a method of using a fastener. At least a portion of the surface of the fastener is placed in contact with tissue. The fastener may be placed in contact with an outer surface of the tissue and/or the inner portion of the tissue. A portion of the surface of the fastener may be flat, convex, or concave. A convex portion of the fastener may be placed in contact with a concave portion of the tissue. A flat portion of the fastener may be placed in contact with a flat portion of the tissue. A concave portion of the fastener may be placed in contact with a convex portion of the tissue. In these configurations, the shaped portions of the fasteners mate with the tissue.

In accordance with yet another aspect of the present invention, a fastener assembly is provided. The assembly includes a plurality of fastener members, each fastener member having at least one channel extending therethrough. A plurality of connecting members links the fastener members to each other. The fastener members may be linked together end to end, side to side, or end to side. When linked together, the fastener members may form a linear, circular, rectangular, J, L, or U configuration. The connecting members may be hinges, pins, ball and socket, interconnecting loops, hooks, flexible filaments and/or rigid members. There may be two or more connecting members which link adjacent fastener members. The channels of the fastener members may be generally transverse to the longitudinal axis of the fastener member. Each fastener member may include two or more channels, and the channels may be generally parallel to each other.

Furthermore, a fastener strip or assembly is provided. The fastener strip or assembly includes a plurality of fastener members disposed on a flexible strip. Each fastener member has at least one channel extending therethrough. The channel may be generally transverse to the longitudinal axis of the fastener member. The fastener members are positioned on the flexible strip to form a linear, circular, rectangular, J, L, and/or U configuration. The fastener members may be affixed to the upper surface of the flexible strip. The fastener members may be affixed to the upper surface of the flexible strip with adhesive. The flexible strip may also have adhesive on its lower or bottom surface for adhesion to tissue. Such adhesives may include cyanoacrylate adhesives, hydrogel adhesives, monomer and polymer adhesives, fibrin, polysaccharide, Indermil® or any other biocompatible adhesive. The flexible strip may be bioabsorbable, bioerodible, degradable, biodegradable, expandable, and/or hydrophilic.

There is also provided a method for using a fastener assembly. The fastener assembly is positioned against tissue. A suture or sutures are positioned within the tissue and through the suture assembly to secure the assembly to the tissue. In one embodiment, the assembly is placed over an incision in the tissue. The fastener members are positioned such that channel of the fastener members are located on each side of the incision. A suture or sutures are positioned within the portions of tissue on opposite sides of the incision and through the fastener assembly. The suture or sutures are tensioned and secured with the fastener members. The type and configuration of the fastener assembly is determined with respect to the shape or configuration of the tissue. The shape of the incision also determines the shape of the fastener assembly.

In accordance with a further aspect of the present invention, a total disc replacement implant is provided. The implant includes a superior or upper portion made of a rigid material. The upper surface of the superior portion is configured to adjoin to a cut portion of a superior or upper vertebra. The implant also includes an inferior or lower portion made of a rigid material. The lower surface of the inferior portion is configured to adjoin to a cut portion of an inferior or lower vertebra. The implant further includes a middle portion made of a flexible material. The middle portion is affixed to the lower surface of the superior portion and the upper surface of the inferior portion.

The superior and inferior portions of the implant may include polymeric, composite, metallic, ceramic, and expandable material. The portions may also include synthetic bone and body tissue like bone, collagen, cartilage, and ligaments. The portions may also be bioabsorbable, bioerodible, degradable, and biodegradable. The middle portion of the implant may include rubber, gel, foam, polymer, collagen, and body tissue. The total disc replacement implant may be made of a plurality of components; that is, the implant may be modular. The components may be connected with each other to form the implant. The components may mechanically interlock with one another. Each component may have a size approximately the same as the length of the incision through which the components are inserted.

In addition, there is provided a method for total disc replacement. An incision is made through tissue for access to the spine. The dimensions of the incision may be minimized to reduce trauma to surrounding tissue like muscle, ligaments, tendons, and cartilage. The vertebra located superior to the damaged disc being replaced is cut. The cut may be made on the lower or bottom portion of the superior vertebra. The cut may be planar or multiplanar. The superior vertebra may be cut without disturbing or at least minimally disturbing the adjacent ligaments, cartilage, and muscles. The cut may be angled to avoid damaging or loosening the spinal ligaments like the anterior and posterior longitudinal ligaments.

The vertebra located inferior to the disc being removed is cut in a similar manner, except the upper surface of the inferior vertebra is cut. Once cut, the cut portions of vertebrae and the intervertebral disc are removed through the incision. The cut vertebrae are further prepared for receiving an implant. The total disc replacement implant or modular implant is positioned between the cut superior and inferior vertebrae. A modular implant may be positioned one component at a time or already assembled. The implant is anchored to the surrounding tissue like the adjacent vertebral bodies. Any ligaments, muscles, cartilage, tendons, or other body tissue cut or damaged during the procedure is repaired prior to closing the incision. Finally, the incision is approximated.

In accordance with another aspect of the present invention, a tissue alignment sleeve is provided. The sleeve includes a tubular member having a wall. The interior surface of the wall is generally smooth. The exterior surface of the wall includes means for gripping and creating friction. The gripping means may include threads, a plurality of raised regions, and a plurality of circumferential elevated areas or rings. The wall may include a plurality of openings for tissue ingrowth and outgrowth. The wall may include one or more longitudinal slits such that the tubular member or sleeve may be bendable to increase and decrease the diameter of the sleeve.

There is further provided a method of using a tissue alignment sleeve. A channel is created in tissue. The sleeve is positioned within the tissue. The gripping or friction means of the sleeve holds the sleeve within the tissue. The tissue may include first and second portions. When positioned within the first and second portions of the tissue, the portions are aligned and maintained in position relative to each other. The first and second portions may be portions of bone on opposite sides of a fracture. The portions may be tissue of a body joint. The portions may be bones of a joint located on opposite sides of the joint, such that when the sleeve is positioned, movement of the joint is restricted.

A sleeve with at least one longitudinal slit may be positioned with the channel created in tissue. The diameter of the sleeve may be decreased by closing the gap in the longitudinal slit. In a decreased diameter, the sleeve may be inserted into the channel. Once positioned, the diameter of the sleeve may be increased thereby engaging the gripping means with the tissue. A suture or sutures may be placed through the lumen of the sleeve to secure tissue located at the ends of the sleeve. After the sleeve has gripped the adjacent tissue with the gripping means, therapeutic substances or graft material (autogenic, allogenic, xenogenic, or synthetic) may be packed into the tubular member.

In accordance with a further aspect of the present invention, a method for stabilizing an implant is provided. A first fastener is positioned in contact with tissue located adjacent the implant. A second fastener is positioned in contact with tissue located adjacent the implant generally opposite the first fastener. A suture is placed between the fasteners and in contact with the implant. The suture is tensioned, and the fasteners are secured to the tensioned suture such that the suture transmits force to the implant. The suture may be positioned in contact with the surface of the implant. The suture may also be positioned within the implant.

In addition, a method for stabilizing an implant within a body is provided. A first fastener is positioned in contact with the implant. A second fastener is positioned in contact with tissue located adjacent the implant. A suture is placed between the fasteners. The suture is tensioned, and the fasteners are secured to the tensioned suture to anchor the implant to the tissue. The first fastener may be positioned within the implant or on the surface of the implant. The suture may be placed against or within the implant.

In accordance with another aspect of the present invention, there is provided a method for anchoring an implant for directional expansion within the body. A first fastener is positioned in contact with the first side of an expandable implant. A second fastener is positioned in contact with tissue located adjacent a second side of the implant which is opposite the first side. A first suture is positioned between the fasteners and tensioned. The first suture is secured with the first and second fasteners. In this configuration, the first side of the expandable implant is restricted from expanding, but all other sides of the implant can expand.

For further restriction of expansion, a third fastener is positioned in contact with the second side of the implant. A fourth fastener is positioned in contact with tissue located adjacent the first side of the implant. A second suture is positioned between the third and fourth fasteners. The second suture is tensioned and secured with the fasteners. The second side of the implant is restricted from expanding. To further restrict expansion of the implant, more fasteners and sutures may be positioned as previously described such that the implant is limited to expansion in one, two, or more directions.

The sutures may be positioned in contact with the expandable implant such that the sutures transmit force to the implant thereby anchoring the implant and further restricting expansion.

In accordance with a further aspect of the present invention, a device for anchoring an implant is provided. The device includes a pouch dimensioned and configured for receiving an implant. The pouch has an access port for inserting the implant. At least one anchoring point is connected with the pouch. The device may further include a flap attached to the pouch for closing the access port. The implant may be expandable, and when positioned in the pouch, the implant generally expands primarily in the direction of the access port. The pouch may include a plurality of access ports. An expandable implant placed in a pouch with a plurality of access ports expands primarily in the directions of the access ports.

In accordance with another aspect of the present invention, there is provided a method for repairing a ligament. A fastener is positioned in contact with the ligament adjacent the first side of a damaged region of the ligament. Another fastener is positioned in contact with the ligament adjacent a second side of the damaged region which is generally opposite the first side. A suture is positioned between the fasteners. The suture is tensioned and secured with the fasteners such that the ligament is tightened. The suture may be positioned through the ligament. The suture may also be positioned through tissue adjacent the damaged area. The tissue may be spine tissue such as one or more vertebrae and one or more intervertebral discs. The ligament may be a ligament of the spine such as the anterior or posterior longitudinal ligament, or any of the previously identified ligaments. The damaged region may be a loosened ligament area, a torn ligament area, or a missing ligament area.

Furthermore, a method for reconstructing a ligament is provided. A tissue graft is positioned adjacent a damaged region of the ligament. A first fastener is positioned in contact with the tissue graft on a first side of the damaged region. A second fastener is positioned in contact with the tissue graft on a second side of the damaged region which is generally opposite the first side. A suture is positioned between the fasteners with the suture passing through the tissue graft and ligament. The suture is tensioned and secured with the fasteners to hold the tissue graft against the ligament. The tissue graft may include ligamentous tissue or bone tissue. The ligament may be a ligament of the spine. The suture may be positioned within tissue located adjacent the ligament. The tissue may be spine tissue including one or more vertebrae and one or more intervertebral discs.

Moreover, there is provided another method for reconstructing a ligament. A tissue graft is positioned adjacent a damaged region of the ligament. A first fastener is positioned in contact with the tissue graft on a first side of the damaged region. A second fastener is positioned in contact with tissue adjacent the ligament. A suture is positioned between the fasteners with the suture passing through the tissue graft and ligament. The suture is tensioned and secured to the fasteners such that at least a portion of the tissue graft is held to the ligament. The tissue graft may include ligamentous tissue or bone tissue. The ligament may be a ligament of the spine like the anterior or posterior longitudinal ligament. The suture may be positioned within the tissue adjacent the ligament. The tissue may be spine tissue including one or more vertebrae and one or more intervertebral discs.

BRIEF DESCRIPTION OF THE SEVERAL VIEWS OF THE DRAWINGS

A more complete understanding of the present invention, and the attendant advantages and features thereof, will be more readily understood by reference to the following detailed description when considered in conjunction with the accompanying drawings wherein:

FIGS. 2A-2G shows a plurality of embodiments of tissue alignment sleeves;

FIG. 3 illustrates the repair of the annulus of an intervertebral disc as well as stabilization of the spinal joint;

FIG. 4 illustrates a total intervertebral disc replacement implant;

DETAILED DESCRIPTION OF THE INVENTION

Figure 1A:
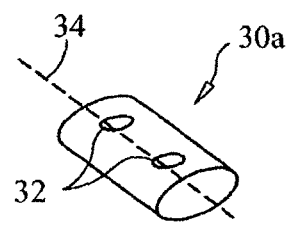
FIGS. 1A-1H illustrate multiple embodiments of fasteners and fastener assemblies.

The devices and methods of the present invention provide for the repair, reconstruction, augmentation, and securing of tissue and/or implants during a surgical procedure and "on the way out" after the surgical procedure has been performed but before the skin incision has been closed. Tissue at and around the operation site and tissue between the operation site and skin incision is rebuilt so that tissue-function may be at least partially restored and the operation region may be stabilized for enhanced healing.

The devices used to repair, reconstruct, augment, and/or secure tissue or implants may be any biocompatible fastener described herein or found in the prior art. Examples of fasteners, implants, and their methods of employment may be found in U.S. Pat. Nos. 5,163,960; 5,403,348; 5,441,538; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,086,593; 6,099,531; 6,159,234; 6,368,343; 6,447,516; 6,475,230; 6,592,609; 6,635,073; and 6,719,765. Other fastener types are disclosed in U.S. patent application Ser. Nos. 10/102,413; 10/228,855; 10/779,978; 10/780,444; and 10/797,685. The above cited patents and patent applications are hereby incorporated by reference.

The fasteners may be, but are not limited to, degradable, biodegradable, bioerodible, bioabsorbable, mechanically expandable, hydrophilic, bendable, deformable, malleable, riveting, threaded, barded, bubbled, laminated, coated, blocking, pneumatic, one-piece, multi-component, solid, hollow, polygon-shaped, pointed, self-introducing, and combinations thereof. Also, the fasteners may include, but are not limited to, metallic material, polymeric material, ceramic material, composite material, body tissue, synthetic tissue, hydrophilic material, expandable material, compressible material, heat bondable material, and combinations thereof The fasteners of the present invention may be linear fixation fasteners. Such fasteners secure tissue or an implant with access to only one side of the tissue or implant. Generally, the fastener is advanced through the tissue or implant, usually through a pre-made passage or without a passage when the fastener is self-introducing. Once placed through the tissue or implant, a distal portion of the fastener expands, biases outward, or changes configuration such that the distal portion prevents the fastener from being pulled back out of the tissue or implant. The proximal portion of the fastener is secured thereby anchoring the tissue or implant. Examples of linear fixation fasteners are further disclosed in the incorporated references.

The methods and devices of the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured during and "on the way out" following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

Exemplary Fasteners

The following Examples 1 through 8 which illustrate uses of the present invention are for illustrative purposes and are not limiting examples. As mentioned above, any fastener disclosed herein or incorporated by reference may be used with the exemplary methods. To simplify the disclosure of the present invention, a limited number of fastener types will be used to illustrate the exemplary methods. For example, the fasteners disclosed in U.S. Pat. No. 5,921,986 will be used to represent any disclosed or known fastener.

As described in the above-mentioned patent, the fasteners may be placed against tissue, and a suture may be looped through the tissue with the ends of the suture positioned within the fasteners. The suture is tensioned, and the ends of the suture are secured using a knot or any other suitable means for maintaining the tension of the suture between the fasteners. The tensioning of the suture, or similar cable, pin, thread, etc., may be controlled and monitored with sensor technology, like a magnetic sensor, which may unload the pressure if necessary. Other known tensioning apparatus may also be utilized. For example, the tensioning system may be spring loaded, pneumatic, electrical, pisoelectric, and magnetic. The tensioning system may be connected with an introducer or cannula or may be part of a fastener or implant. The tensioning system may include a read-out display outside the body. The read-out display may receive tension data through radiofrequency energy, infrared energy, or other suitable energy source.

Additionally, two or more fasteners may be utilized to secure body tissue and/or an implant. When two fasteners are used, one fastener is placed against or within one tissue area and the second fastener is placed against or within another tissue area. The suture is looped through one fastener while the ends of the suture are positioned within the second fastener. The suture is tensioned and the ends fastened with a knot or fastened using a device or method disclosed herein or incorporated by reference. In this configuration, the suture includes two generally parallel legs or portions located between the fasteners. Furthermore, when two fasteners are used, a single suture may be employed leaving only one leg between the fasteners. In this configuration, each end of the suture is positioned in different fasteners. The suture may be tensioned and the ends secured. It is further contemplated that the fasteners and sutures may be inserted through a passage in the tissue or implant. For example, a passage may be drilled through tissue or implant for insertion of the fastener or suture. With the fastener in place, these passages may be packed or filled with tricalcium phosphate (TCP), calcium phosphate, a thermal polymer, polymethyl methacrylate (PMMA) with hydroxyaptite (HA), polylactic acid (PLA) with HA, and other suitable materials. These materials may harden within the passage and would provide additional stabilization of the tissue or implant.

Figure 1B:
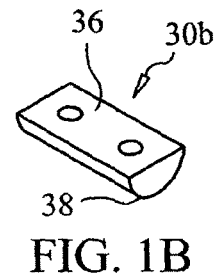
Figure 1C:
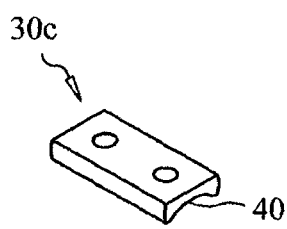
Figure 1D:
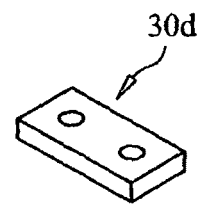

FIGS. 1A-1F illustrate exemplary fasteners 30 with at least one channel 32. In an exemplary embodiment, FIG. 1A shows a generally cylindrical shaped fastener 30a. Two channels or slots 32a for receiving a suture or other similar filament extend through the fastener 30a and are generally perpendicular to the longitudinal axis 34 of the fastener 30a. FIG. 1B shows a generally half cylindrical shaped fastener 30b. The fastener 30b includes a generally flat surface 36 on one side and an arched surface 38 on the other side. The flat surface 36 may be placed against the tissue or implant to provide increased contact area. FIG. 1C shows a cylindrical shaped fastener 30c with a hemispheric or concave surface 40 on one side. This surface 40 may be placed against an implant or tissue, like a bone, which has a convex surface, so that the concave surface 40 of the fastener 30c and the convex surface of the tissue/implant are in contact. FIG. 1D shows a generally rectangular fastener 30d. The fastener 30d may have a thickness which minimizes protrusion of the fastener 30d from the outer surface of the tissue or implant which it is positioned against.

Although the exemplary fasteners have been described as generally longitudinal members, it is also contemplated that the fasteners can take the form of a square, oval, sphere, button, or any other suitable configuration.

Figure 1E:
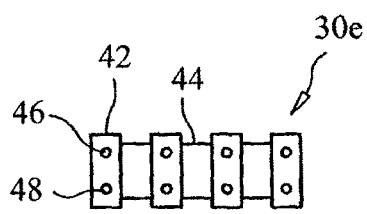

FIG. 1E shows a fastener assembly 30e having a plurality of fastener members 42 positioned generally parallel to each other with connecting members 44 between them. The fastener members 42 may take the form of any shape described previously or incorporated by reference. The connecting members 44 attach the fastener members 42 to each other. The connecting members 44 may be hingedly or pivotally connected with the fastener members 42 to allow the fastener assembly 30e to flex or bend. Alternatively, the connecting members 44 may be made of a flexible material such as a suture, wire, cable, or thread, which could flex or bend. In an exemplary embodiment, the channels 32e of the fastener members 42 are positioned such that a row of channels 46 are aligned over one portion of tissue located on one side of an incision while another row of channels 48 are aligned over the other portion of the tissue located on the opposite side of the incision. Multiple sutures may be used with the fastener assembly for securing tissue or an implant.

Figure 1F:
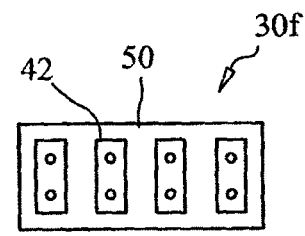

Alternatively, the fastener members 30e may be connected with one another with a flexible strip 50. As seen in FIG. 1F, four fastener members 42 are affixed to the flexible strip 50 and are generally parallel to each other and spaced apart from each other. The strip 50 may be handled and placed against tissue or an implant thereby positioning all the fastener members 42 at about the same time. In this regard, the flexible strip 50 can be made of or include graft material such as collagen, demineralized bone, etc. The flexible strip 50 may be expandable, hydrophilic, bioabsorbable, bioerodible, degradable, biodegradable, or combinations thereof. It may include a therapeutic substance such as antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, germicides, and combinations thereof.

The flexible strip 50 may also include an adhesive on one side to adhere the fastener members 42 to the strip 50 and may further include adhesive of the other side to adhere the strip 50 to tissue or implant. Such adhesives may include cyanoacrylate adhesives, hydrogel adhesives, monomer and polymer adhesives, fibrin, polysaccharide, Indermil® or any other biocompatible adhesive.

Figure 1G:
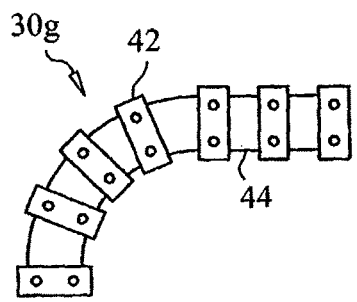
Figure 1H:
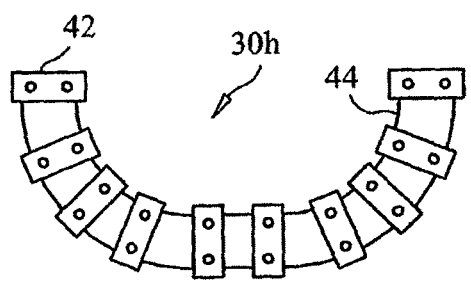

FIG. 1G shows another fastener assembly 30g of the present invention. This fastener assembly 30g is generally L-shaped or J-shaped. Like the fastener assemblies of FIGS. 1E and 1F, the fastener members 42 of FIG. 1G may be attached to one another with connecting members 44 or with a flexible strip 50. FIG. 1H shows a U-shaped fastener assembly 30h for closing a U-shaped incision in tissue, like those frequently made in the annulus. The rows of channels 46 and 48 of the fastener members 42 are arranged as previously described, with one line of channels 46 on one side of the incision and the other line of channels 48 of the other side of the incision.

The type and shape of the incision determine the size and configuration of the fastener assembly used. For example, a U-shaped incision could be closed with a U-shaped fastener assembly 30h, and an L-shaped incision could be closed with an L-shaped fastener assembly 30g. The suture or sutures used with the fastener assemblies may be tensioned and secured with a knot, or alternatively may be secured with devices and methods described herein and those incorporated by reference.

The exemplary fasteners may be utilized with one or more sutures, filaments, cables, or other similar implant. Generally, one suture may be used for the fasteners of FIGS. 1A-1D when only one fastener is employed. When two or more fasteners of FIGS. 1A-1D are used, multiple sutures may be employed. Similarly, the fasteners of FIGS. 1E-1H may use multiple sutures. The ends of sutures may be placed through the channels of the fastener members, and the sutures tensioned. Alternatively, a single suture could be used. That is, the single suture may be threaded in and out of the channels of the fastener members to secure tissue or an implant.

The exemplary fasteners and fastener assemblies of the present invention may be formed of any natural or artificial material. For example, they may be formed from material which is polymeric, metallic, composite, ceramic, or combinations thereof. Furthermore, the fasteners and assemblies may be made of body tissue including bone, collagen, cartilage, ligaments, or tissue graft material like xenograft, allograft, and autograft. They may be bioabsorbable, bioerodible, degradable, biodegradable, mechanically expandable, hydrophilic, and combinations thereof. The fasteners and assemblies may be made from a porous matrix or mesh of biocompatible and bioresorbable fibers acting as a scaffold to regenerate tissue.

The fasteners and assemblies may also be made of or have a coating made of an expandable material. The material could be compressed then allowed to expand once sutured to tissue or an implant. Alternatively, the fastener and assembly material could be hydrophilic and expand when it comes in contact with liquid. Examples of such expandable materials are desiccated body tissue, foam, and expandable polymers.

Furthermore, the fasteners, fastener assemblies, and implants described herein and incorporated by reference may include therapeutic substances to promote healing. These substances could include antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener or implant. Alternatively, the therapeutic substances may be impregnated or coated on the fastener or implant. Time-released therapeutic substances and drugs may also be incorporated into or coated on the surface of the fastener or implant. The therapeutic substances may also be placed in a bioabsorbable, degradable, or biodegradable polymer layer or layers.

The sutures of the present invention may be made of metallic material, non-metallic material, composite material, ceramic material, polymeric material, copolymeric material, or combinations thereof. The sutures may be degradable, biodegradable, bioabsorbable, or non-biodegradable. Examples of suture materials are polyethylene, polyester, cat gut, silk, nylon, polypropylene, linen, cotton, and copolymers of glycolic and lactic acid. In an exemplary embodiment, the sutures are flexible or bendable. They may be threadlike, monofilament, multifilament, braided, or interlaced. The sutures may have a coating of therapeutic substances or drugs. For example, the sutures may include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

FIGS. 2A-2C illustrate exemplary embodiments of another fastener 52. The fastener or tubular member or sleeve 52a in FIG. 2A is generally tubular shaped having a wall 54 with an inner surface 56 and an outer surface 58. The inner surface 56 defines a lumen 60 which is dimensioned and configured for receiving a suture, cable, K-wire, or similar device. In another embodiment, FIG. 2B shows a sleeve 52b with a slit 62 through the tubular wall 54. The slit 62 allows the sleeve 52b to be decreased in diameter for implantation and increased in diameter after implantation for proper alignment of the implantation site. In a further embodiment, the sleeve 52c of FIG. 2C includes two slits 62 in the tubular wall 54 thereby forming two semi-tubular members. The semi-tubular members may be placed separately at the implantation site then aligned to form a complete tubular member. In another embodiment, the tubular member is a solid member.

The tubular member may be flexible to enable the tubular member to be inserted into a nonlinear passage through the bone. The tubular member may be formed of metallic material, composite material, ceramic material, polymeric material, or combinations thereof. The tubular member may be made from a degradable, biodegradable, bioerodible, or bioabsorbable material, such as a polymer, composite, or ceramic. The tubular member may also include a therapeutic substance to form a composite tubular member, or the therapeutic substance may be coated onto the tubular member. Furthermore, therapeutic substances or graft material (autogenic, allogenic, xenogenic, or synthetic) may be packed into the tubular member.

Additionally, the outer surface 58 of the tubular member 52 may include a friction or gripping means. FIG. 2D shows a portion of the outer surface 58 of the tubular member with threads 64. In FIG. 2E, the outer surface 58 includes raised pebbles, or bumps 66. FIG. 2F illustrates raised ridges or hills 68 around the outer surface 58. In addition to a friction means on the outer surface of the tubular member, the wall of the sleeve may include openings 70 for tissue ingrowth, as shown in FIG. 2G. It is contemplated that any of the fasteners, fastener assemblies, and implants disclosed herein and incorporated by reference may also include a friction or gripping means as described above.

It is further contemplated that tissue and implants may be secured with biologic adhesive, or fasteners disclosed herein and incorporated by reference may be used with the biologic adhesive. Such adhesives may include cyanoacrylate adhesives, hydrogel adhesives, monomer and polymer adhesives, fibrin, polysaccharide, Indermil® or any other biocompatible adhesive. For example, tissue scaffolds and tissue welding fasteners disclosed herein or incorporated by reference may be used with adhesive and an energy source, like ultrasound, RF, laser, electromagnet, ultraviolet, infrared, electro-shockwave, or other suitable energy source, to activate or deactivate the adhesive.

Example 1-Intervertebral Disc Repair

As previously described, the present invention provides devices and methods for fastening body tissue and/or an implant. One example is the fastening or repair of ligamentous tissue. Ligamentous tissue is found, among other locations, within intervertebral discs of the spinal column. The spinal column is formed from a number of vertebrae which are separated from each other by intervertebral discs. The intervertebral discs stabilize and distribute force between the many vertebrae. As used herein, "spinal joint" or joint of the spine includes this intervertebral space.

Generally, intervertebral discs are made of a soft, central nucleus pulposus surrounded by a tough, woven annulus fibrosus. Herniation of a disc is a result of a weakening in the annulus. Symptomatic herniations occur when weakness in the annulus allows the nucleus pulposus to bulge or leak posteriorly toward the spinal cord and major nerve roots. One treatment of a herniated, displaced, or ruptured intervertebral disc is a discectomy. This procedure involves removal of disc materials impinging on the nerve roots or spinal cord posterior to the disc. Depending on the surgeon's preference, a varying amount of nucleus pulposus is removed from within the disc space either through the herniation site or through an incision in the annulus. In addition to a discectomy, other surgical procedures where the present invention may be used include a vertebroplasty and kyphoplasty.

FIG. 3 illustrates an exemplary embodiment of repairing an intervertebral disc 80. The disc 80 is located between a superior vertebra 82 and an inferior vertebra 84. During a discectomy, an incision 86 is made through the annulus fibrosus 88 for the removal of all or a portion of the nucleus pulposus 90. After the appropriate amount of the nucleus 90 has been removed, the incision 86 is approximated. In one embodiment showing the closing of the incision 86, a fastener 30 is positioned generally transverse to the incision 86. The fastener 30 is positioned on the outer surface of the annulus 88 with one channel 32 on one side on the incision 86 and the other channel 32 on the other side of the incision 86. A suture 100 is positioned through the portions of annulus 88 located on opposite sides of the incision 86 in a generally U-shaped, looped, or curved configuration. The ends of the suture 100 are placed within the channels 32 of the fastener 30 and tensioned to draw together the two portions of the annulus 88 on opposite sides of the incision 86. The suture 100 is secured to the fastener 30 with a knot or other means disclosed herein or incorporated by reference. Depending on the length of the incision, a plurality of fasteners and sutures may be used to fully close the incision.

One or more additional incisions 86 in the annulus 88 may be necessary for increased access to the nucleus 90. These other incisions will also need to be approximated. As seen in FIG. 1, one fastener 30 is placed on one side of the incision 86 generally parallel to the incision 86. A second fastener 30 is positioned on the other side of the incision 86. Closure of the incision 86 is accomplished by placing a suture or sutures 100 through the annulus 88 so that the annulus portions on opposite sides of the incision 86 are drawn together when the suture 100 is tensioned. The ends of the suture are secured by the fasteners 30. Depending on the length of the incision, more than two fasteners may be utilized to approximate the incision. The closure of the incision enhances the natural healing and reconstruction of the annulus wall.

While the incisions of FIG. 3 are generally linear, other incision configurations may be made for increased accessibility through the annulus. For example, the incision may be circular, L-shaped, U-shaped, C-shaped, J-shaped, etc. Different configurations and types of fasteners illustrated in FIG. 1 may be used to close these non-linear incisions. Furthermore, these incisions may be made anywhere along the annulus (posterior, anterior, or sides) or between the annulus and vertebral body.

It is further contemplated that access to the nucleus pulposus may be obtained through a vertebral body. A channel(s) or passage(s) 92 may extend from the outer side surface of the vertebral body to the adjacent nucleus. The channel may be formed with a bone drill bit and/or a tissue harvesting device as described in U.S. Pat. No. 5,269,785 entitled Apparatus and Method for Tissue Removal, which is hereby incorporated by reference. The nucleus pulposus material may be fully or partially removed through the channel 92. Means for removing the material may include suction, scrapper, scooper, syringe, or other similar device. When no new material is required to be implanted in the region where the nucleus pulposus material was removed, the physician may close the channel 92 with graft material such as autograft material, allograft material, and/or other implantable materials disclosed herein. Alternatively, a plug/seal 93 made of metal, polymer, composite, or ceramic may be inserted into the channel 92 at either end of the channel or at both ends of the channel. The plug 93 may be removable for gaining access to the nucleus pulposus during a subsequent surgery. In this method, the annulus fibrosus is not incised, punctured, or weakened thereby reducing the healing time of the disc.

Depending on the severity of herniation or damage to the disc, nucleus pulposus replacement material or a nucleus pulposus prosthesis may be positioned between a superior vertebra and inferior vertebra. One or more incisions may be made through the annulus for access to the nucleus. The nucleus pulposus may be removed, and the replacement material or prosthesis may be inserted. Alternatively, the nucleus pulposus also remain in place with the replacement material or prosthesis positioned next to or along with the existing nucleus pulposus. Furthermore, the nucleus pulposus can be removed, conditioned or treated, and then re-implanted either alone or with a replacement material. In this regard, the temporarily removed nucleus pulposus can serve as a scaffold seeded with cells or treated with a growth factor or any other of the therapeutic agents disclosed herein. The fasteners and sutures of the present invention may be used to approximate the annulus incisions. Any number of fasteners may be used to fully close the incision.

The nucleus pulposus replacement material or prosthesis may also be positioned between the superior and inferior vertebrae through a vertebral body. As mentioned previously, a passage or channel may be made through the vertebral body extending from the outer surface to the adjacent nucleus pulposus. All, some, or none of the existing nucleus pulposus may be removed prior to insertion of the replacement material or prosthesis. In an exemplary embodiment, the replacement material is injected through the incision or channel in the vertebra and into the nucleus pulposus area. This material may be flowable for injection then once injected may become less flowable to form a gel-like material or, alternatively, may become generally solid to form a rubber-like material. Additionally, the nucleus pulposus replacement material may be flowable or injected into a balloon or bladder which may be positioned between adjacent vertebral bodies.

In another embodiment, the replacement material or prosthesis may be rubber-like or gel-like pellets having a configuration which allows them to be passed through the incision or channel. The replacement material or prosthesis may be expandable so that, once inserted, it can fill the implant area. The materials or prosthesis may include an adhesive and/or therapeutic substances, like antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Surgery of the intervertebral disc may leave the spine with increased motion or shear which can cause further disc failure, facet hypertrophy, or arthritis of the facet joints. To stabilize the repaired intervertebral disc "on the way out," the devices and methods of the present invention may be utilized. Flexible fixation of tissue at and near the operation site may allow compression of tissue and limited motion of the repaired intervertebral disc allowing ligaments, the annulus fibrosis, interspinous ligaments, and other soft tissue to properly heal. Stabilizing one vertebral body to another vertebral body under compression would still allow for some range of motion of the joint yet prevent disc degeneration.

The vertebral bodies may be stabilized anteriorly and/or posteriorly or with a hybrid approach such as an anterior-lateral or posterior-lateral approach. For example, on the anterior side of the spine, two fasteners 30 are positioned to secure the ends of a suture 100 placed through the intervertebral disc 80 and through adjacent vertebrae 82 and 84 in a curved or looped configuration. Two other fasteners 30 are positioned against or within the vertebrae 82 and 84 to hold the ends of a suture or sutures 100 placed through the disc 80 and through the adjacent vertebrae 82 and 84 in a generally straight configuration. Two more fasteners 30 are positioned against or within two vertebrae 102 and 104 located a distance from the repaired disc 80. A suture or sutures 100 are placed between these vertebrae 102 and 104 and tensioned. These fasteners and sutures provide stability and an enhanced healing environment for the intervertebral disc.

Finally, FIG. 3 illustrates another exemplary embodiment for stabilizing tissue around a repaired tissue region. One fastener 30 is positioned against or within an upper spinous process 106 adjacent the repaired disc 80, while another fastener 30 is positioned against or within a lower spinous process 108 also adjacent the repaired disc 80. A suture or sutures 100 are placed between the fasteners 30 and tensioned. This configuration and placement of fasteners and sutures limits or prevents the movement of the repaired disc.

Example 2-Intervertebral Disc Replacement

A damaged intervertebral disc may require replacement instead of just minor repair. The disc may be replaced with a prosthetic disc which may include a biocompatible material such as metal, polymer, composite, ceramic, or combinations thereof. FIG. 4 illustrates a total intervertebral disc replacement using the devices and methods of the present invention. While a disc replacement is shown and described below, it is contemplated that any skeletal region, like a joint, may be fitted with an implant, and the implant fastened and stabilized with the sutures, fasteners, and methods disclosed herein and incorporated by reference. For example, a knee replacement component may be affixed to the femur, tibia, or patella in accordance with the following described methods.

A disc replacement component may be positioned between the lower surface of a superior vertebra and the upper surface of an inferior vertebra. In this configuration, the disc replacement component takes the place of the original intervertebral disc and provides the proper spacing between the vertebrae. Such a disc component may be anchored to the surfaces of the superior and inferior vertebrae with the fasteners and sutures described herein and incorporated by reference.

Alternatively, and as shown in FIG. 4, the disc replacement implant 110 may be larger in height than the normal height of an intervertebral disc. The implant 110 may include upper 112, middle 114, and lower 116 sections. The upper and lower sections 112 and 116 are made of a biocompatible material which allows integration of the bone tissue of the vertebral bodies. This material may be polymeric, composite, metallic, ceramic or combinations thereof. Furthermore, the material may be body tissue including bone, collagen, cartilage, ligaments, or tissue graft material. The material may be bioabsorbable, bioerodible, degradable, and/or biodegradable.

The upper and lower sections 112 and 116 of the disc replacement component 110 may include therapeutic substances, like antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides. Finally, the upper and lower sections 112 and 116 may include an expandable material. This material could be compressed then allowed to expand once implanted. Alternatively, the material could be hydrophilic and expand when it comes in contact with liquid. Examples of such expandable materials are desiccated body tissue, foam, and expandable polymers.

The middle section 114 of the disc implant 110 includes a flexible or resilient material. The middle section 114 functions as the original intervertebral disc. Materials which may be used in the middle section 114 include rubber, gel, foam, polymer, collagen, body tissue, or other suitable material. The middle section 114 may also include an expandable material. Furthermore, therapeutic substances such as antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides may be included in the middle section 114 of the disc replacement implant 110.

The disc implant 110 is positioned as follows. The superior vertebra 118 may be cut to receive the upper section 112 of the disc implant 110, while the inferior vertebra 120 may be cut to receive the lower section 116 of the implant 110. The cuts may be made from any side of the vertebral body. However, it is preferred that cutting the vertebrae 118 and 120 results in minimal disruption of the surrounding tendons, muscles, nerves, and ligaments, like the anterior and posterior longitudinal ligaments. The cuts may be planar and generally perpendicular to the longitudinal axis of the spine. The cuts may also be multi-planar such that the pedicles and facet joints are not affected or weakened.

The upper, middle, and lower sections 112, 114, and 116 of the implant 110 combine to form a height which when the implant 110 is positioned between the cut portions of the superior and inferior vertebrae 118 and 120, is generally the same height of the normal intervertebral disc and adjacent vertebral bodies. This technique is analogous to a total knee replacement procedure. The femur, tibia, and patella are cut and prepared for implant components. Once affixed, the knee replacement components return the knee joint to its normal height, configuration, and function. The spinal implant 110 of the present invention is similar; it returns the spinal column to its normal height and function.

To secure the disc implant 110 to the cut superior and inferior vertebrae 82 and 84, the sutures, fasteners, and methods of the present invention may be used. As seen in FIG. 4, a fastener 30 is positioned within or against the superior vertebra 82, while a second fastener 30 is placed within or against the upper section 112 of the disc implant 110. A suture 100 positioned between the fasteners 30 is tensioned thereby anchoring the implant 110 to the superior vertebra 82. In addition, a graft 120, like a tissue graft, is positioned over the lower section 116 of the implant 110 and the inferior vertebra 84. Two fasteners 30 with sutures hold the graft 120 in place thereby anchoring the implant 110 to the inferior vertebra 84. To help stabilize the region around the disc implant 110, a first fastener 30 is positioned within or against a spinous process 106, while a second fastener 30 is placed within or against a different spinous process 108. A suture 100 extends between the fasteners 30 and is tensioned to limit movement of the spinous processes 106 and 108 and their relative vertebral bodies.

The disc implant 110 is further anchored to the superior and inferior vertebrae 82 and 84 with fasteners, sutures, and tubular members. Two fasteners 30 are positioned within or against the vertebrae 82 and 84. Two other fasteners 30 are placed within or against the disc implant. Sutures 100 are positioned within tubular members or sleeves 52 that extend between the fasteners. The tubular members 52 may have a thin cylindrical wall which engages the bone of the vertebrae 82 and 84 and material of the implant 110. By inserting the tubular members 52 in such an orientation, the superior and inferior vertebrae 82 and 84 and disc implant 110 are maintained in alignment.

It is also contemplated that the tubular member or sleeve may be placed within ligaments, tendons, muscles, bones, or combinations thereof. For example, the tubular member may be positioned in bones, including transverse process, pedicles, facets, spinous process, posterior arch, odontoid process, posterior tubercle, lateral articular process, uncinate process, anterior tubercle, carotid tubercle, and vertebral body. The tubular member may also be positioned in ligaments, including the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine.

Following intervertebral disc replacement, the spine and surrounding tissue may be become weakened. To stabilize these regions "on the way out," the devices and methods of the present invention may be utilized. Flexible fixation of tissue at and near the operation site may allow compression of tissue and limited motion of the prosthetic intervertebral disc allowing ligaments, the annulus fibrosis, interspinous ligaments, and other hard or soft tissue to properly heal. Stabilizing one vertebral body to another vertebral body under compression would allow for some range of motion of the joint and prevent disc degeneration and reduce the incidence of postoperative pain.

Example 3-Implant Anchoring

The devices and methods of the present invention may be further used to stabilize an implant positioned within the body. In addition to the type of implants previously mentioned, the implant may be an organ, partial organ grafts, tissue graft material (autogenic, allogenic, xenogenic, or synthetic), a malleable implant like a sponge, mesh, bag/sac/pouch, collagen, or gelatin, or a rigid implant made of metal, polymer, composite, or ceramic. Other implants include breast implants, biodegradable plates, metallic fasteners, rods, plates, screws, spacers, cages, compliant bearing implants for one or more compartments of the knee, nucleus pulposus implant, stents, meniscal implants, tissue grafts, tissue scaffolds, biodegradable collagen scaffolds, and polymeric or other biocompatible scaffolds.

Also, fasteners and sutures may be utilized to position bone replacement implants including joint replacement components such as for the knee and hip, drug delivery implants, pain pumps, spinal implants, dental implants, tissue implants, tissue patches such as porcine, bovine, or patches disclosed in U.S. Pat. No. 6,592,625 to Cauthen, and other implants. The previously mentioned patent is hereby incorporated by reference. The implants, fasteners, and sutures may also include cells bonded to their surface. The cells may be bonded with a biocompatible adhesive, such as those describe herein, and/or may be bonded electromagnetically or with vanderwalls forces. While implant anchoring is described below in reference to intervertebral disc implants, it should be understood that the methods described herein may be used for anchoring any implant with the body.

Figure 5:
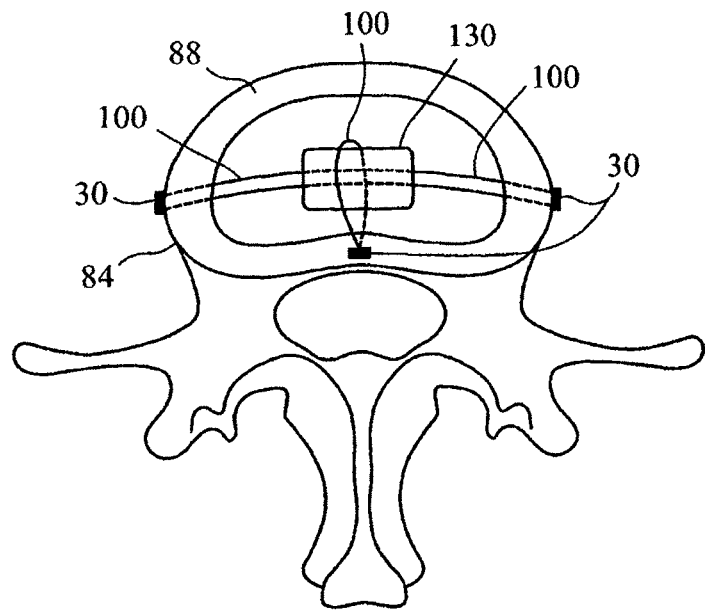
FIG. 5 illustrates an embodiment for the anchoring of an implant.

In FIG. 5, a prosthetic disc implant 130 is positioned between two vertebrae (only one shown) 84. The annulus fibrosis 88 encircles the implant 130. A fastener 30 is placed within the posterior portion of the annulus 88. A suture 100 loops around and/or through the implant 130, and the suture 100 is secured with the fastener 30. Tensioning the suture 100 in this configuration stabilizes the implant 130 by preventing movement of the implant 130 in a posterior-anterior direction. Two other fasteners 30 are positioned against the annulus 88 generally on the sides of the annulus. A suture 100 connects these two fasteners 30 and holds the implant 130 preventing movement in a side-to-side or lateral direction. It is contemplated that the sutures and fasteners used to anchor an implant may extend through or around the implant.

Figure 6:
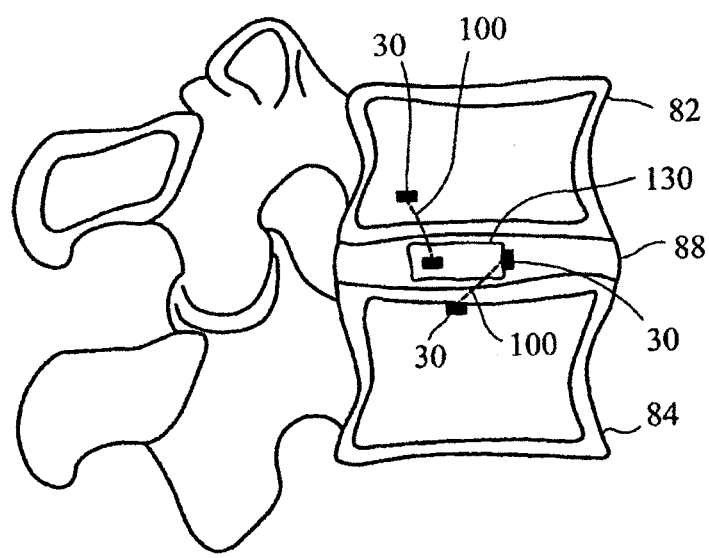
FIG. 6 shows a further embodiment for the anchoring of an implant.

FIG. 6 illustrates a disc implant 130 stabilized between a superior vertebra 82 and inferior vertebra 84. A fastener 30 is positioned within the implant 130 while another fastener 30 is placed within or against the superior vertebra 82. A suture 100 is tensioned between the fasteners 30 to hold the implant 130 to the lower surface of the superior vertebra 82. For added stability, a fastener 30 is placed within or against the inferior vertebra 84 while another fastener 30 is positioned against the implant 130. A suture 100 passes through the implant 130 and the fasteners 30, and the ends of the suture 100 are secured. Any of the methods and devices described herein or incorporated by reference may be used to fasten the ends of the suture.

As previously mentioned, the implant may be any object surgically placed within the body. The implant may be made from various biocompatible materials. Also, the implant may be expandable within the body. A hydrophilic implant may swell or expand by absorbing liquid. A resilient implant may be compressed prior to implantation, then expand once positioned within the body. It is contemplated that an expandable implant may be stabilized using any method and device disclosed herein. In addition, the expandable implant may be held with fasteners and sutures such that expansion of the implant may be directed in a preferred direction or directions. Moreover, electromagnetic pulsed energy may be used to thermally lock a suture to the implant within the body.

Figure 7:
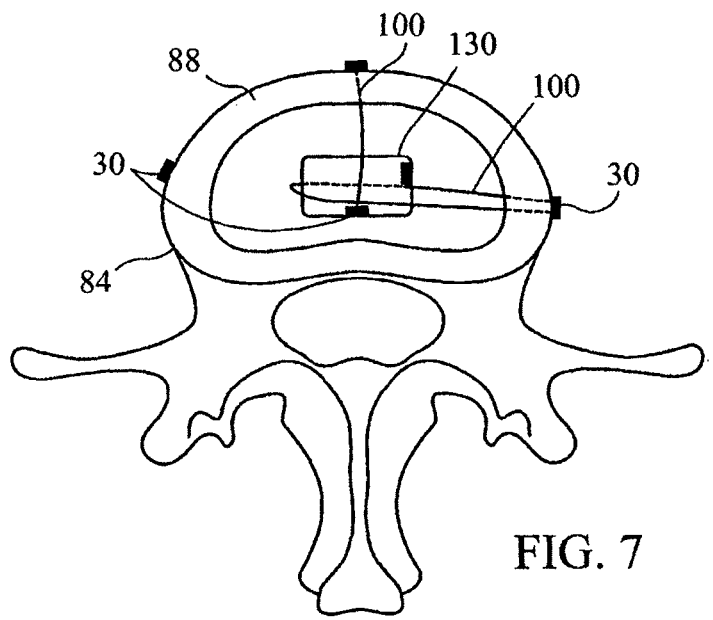
FIG. 7 illustrates anchorage of an expandable implant for directional expansion.
Figure 8A:
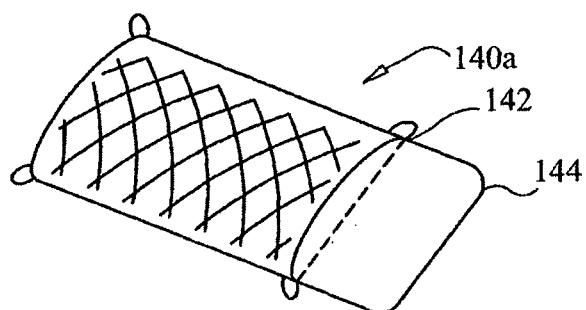
FIGS. 8A-8C show multiple embodiments of implant pouches.

In FIG. 7, an implant 130 is stabilized to a vertebra 84 with multiple sutures and fasteners in a way to allow the implant to expand anteriorly. A first fastener 30 is positioned against the left side of the annulus 88, while a second fastener 30 is placed within or against the right side of the implant 130. A suture 100 extends between the first and second fasteners 30. When tensioned, the suture 100 prevents the implant 130 from expanding to the right while holding the top of the implant 130 as well. A third fastener 30 is positioned against the right side of the annulus 88. A suture 100 is looped around and/or through the implant 130 and secured with the third fastener 30 to thereby prevent the implant 130 from expanding to the left. A fifth fastener 30 is positioned against the anterior side of the annulus 88, while a sixth fastener 30 is place within or against the posterior side of the implant 130. A suture 100 positioned between the fifth and sixth fasteners 30 keeps the implant 130 from expanding in the posterior direction. Given this configuration of sutures and fasteners, the implant 130 is limited to expansion in only the anterior direction. It is contemplated that other configurations of sutures and fasteners may be used to limit the expansion of the implant to one or more directions. That is, the implant may be allowed to expand to the left, right, posterior, anterior, up, down, diagonally, or any combination thereof The present invention also provides an enclosure 140 for stabilizing and anchoring an implant and furthermore to direct expansion of the implant in zero, one, or more desired directions. FIG. 8A illustrates an enclosure (or pouch, bag, sac, etc) 140a for an implant. The implant may be expandable or non-expandable. The pouch 140 may include one or more anchoring points 142. The anchoring points 142 may be placed on any of the corners, edges, or other surfaces so that when anchored the pouch 140 is properly secured at the desired location and orientation. A flap or lid 144 allows access into the pouch 140 for positioning of the implant. The flap 144 may be closed and sealed so the entire implant is enclosed. A pouch that completely encloses an expandable implant would allow the implant to expand omni-directionally until restricted by the pouch. The lip or flap may be resealable such that the material may be added to or removed from the pouch inside the body.

The pouch may be made from any natural or artificial material. For example, it may be formed from material which is polymeric, composite, metallic, ceramic, or combinations thereof. Furthermore, the pouch may be made of or include body tissue including bone, collagen, cartilage, muscle, tendon, ligaments, or other tissue graft material. The material of the pouch may be solid, porous, bioabsorbable, bioerodible, degradable, and/or biodegradable. The pouch may be made from a porous matrix or mesh of biocompatible and/or bioabsorbable fibers or filaments acting as a scaffold to regenerate tissue. The fibers or filaments may be interlaced, braided, or knitted to form the pouch.

The pouch may include or may be filled with therapeutic substances or drugs, like antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides. The pouch may further include or be filled with a gelatin which may contain a therapeutic agent. The gelatin inside the pouch may slowly osmotically leak out into the surrounding tissue.

The pouch may also include an adhesive to bond the pouch to the implant, to bond the pouch to the implantation site, and/or bond the flap to the pouch. Such adhesives may include cyanoacrylate adhesives, hydrogel adhesives, monomer and polymer adhesives, fibrin, polysaccharide, Indermil® or any other biocompatible adhesive. A pouch filled with one or more therapeutic agents may form a drug cocktail implant. The therapeutic agents selected to be inserted within the pouch may be specifically tailored to the needs of the patient. The pouch may be filled outside or within the patient. Once placed within the body, the therapeutic agent may slowly dissolve and exit the pouch through an osmotic member to reach the surrounding tissue.

Figure 8B:
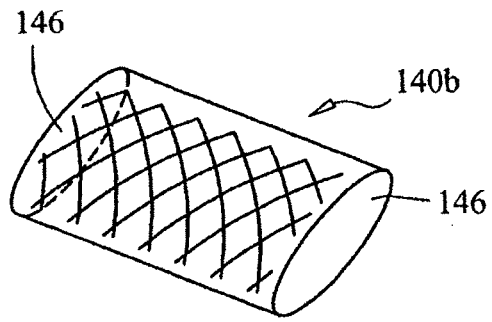
Figure 8C:
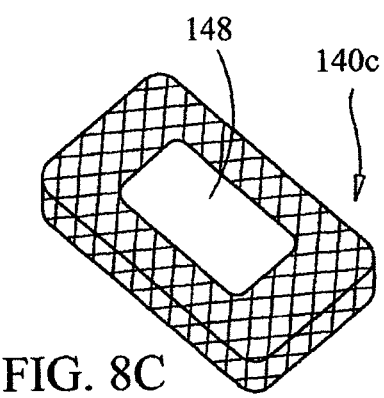

In another exemplary embodiment, FIG. 8B shows a pouch 140b with a bi-directional expansion ports 146 on the left and right sides. When an expandable implant is placed in the pouch 140 and secured at the implantation site, the implant is restricted in expansion in all directions except to the left and right. It is contemplated that the pouch 140 may be designed with one or more expansion ports 146 facing in any direction. In FIG. 8C, the pouch 140c includes a unidirectional expansion port 148. The pouch 140 allows the expandable implant to expand upward. A pouch with an upward or downward pointing expansion port may be particularly useful for prosthetic disc replacement. Once placed in the pouch and positioned between two vertebrae, an expandable implant may expand to increase the space between the vertebrae.

Example 4-Ligament Repair

Instability of joints between bones has long been the cause of disability and functional limitation in patients. Joints of the musculoskeletal system have varying degrees of intrinsic stability based on joint geometry and ligament and soft tissue investment. Ligaments are soft tissue condensations in or around the joint that reinforce and hold the joint together while also controlling and restricting various movements of the joints. When a joint becomes unstable, either through disease or traumatic injury, its soft tissue or bony structures allow for excessive motion of the joint surfaces relative to each other and in directions not normally permitted by the ligaments.

Common problems associated with excessive joint motion are malalignment problems, subluxation of the joint, and possibly joint dislocation. Typically, the more motion a joint normally demonstrates, the more inherently loose is the soft tissue surrounding the joint. A loose ligament or group of ligaments ultimately causes skeletal disorders. However, over tensioning ligaments restricts motion of the joint and can also cause musculoskeletal problems.

The present invention also provides methods of tensioning a ligament (or tendon) or group of ligaments (or tendons) during a surgical procedure and "on the way out" after the surgical procedure to prevent joint instability and reduce pain. These methods can be applied to any ligament in the body, including the ligaments of the knee (like the anterior cruciate ligament and iliotibial band), shoulder, elbow, wrist, hip, ankle, hands, and feet. For illustrative purposes, the methods of the present invention are described with reference to the spine.

When an intervertebral disc becomes herniated and loses nucleus pulposus tissue, the distance between the adjacent vertebrae is reduced from the compression of the annulus and remaining nucleus pulposus. As a result, the spine ligaments may become relaxed. These ligaments may include, but are not limited to, the anterior longitudinal ligament, posterior longitudinal ligament, interspinous ligaments, supraspinous ligament, ligamentum flavum, intertransverse ligament, facet capsulary ligament, ligamentum nuchae, and ligaments of the sacrum and coccyx spine.

Figure 9:
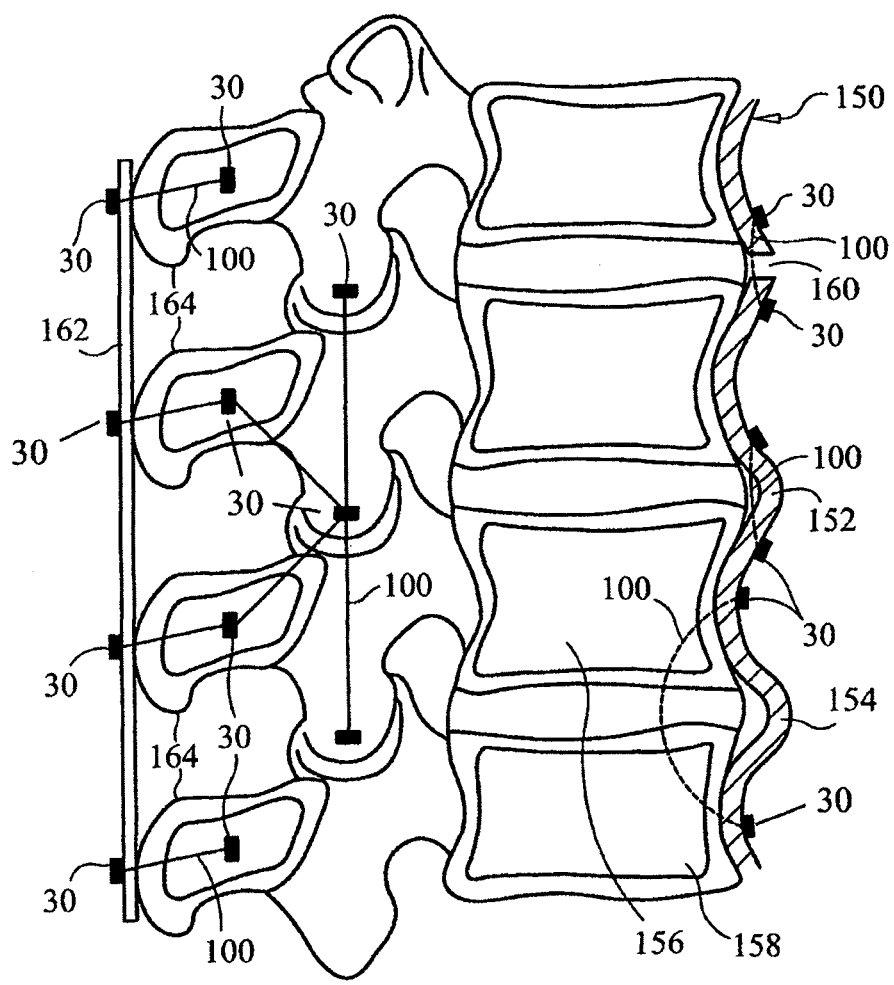
FIG. 9 illustrates ligament repair and stabilization.

FIG. 9 shows an anterior longitudinal ligament 150 which has become weakened. The fasteners and sutures of the present invention may be used to tighten the anterior longitudinal ligament 150 and decrease anteroposterior translation of the adjacent intervertebral discs. It should be understood that the methods described with respect to the anterior longitudinal ligament may also be applied to tightening other ligaments of the body.

A fastener 30 is positioned against the ligament 150 adjacent the upper end of a loosened region 152 of the ligament 150. Another fastener 30 is positioned against the ligament 150 adjacent the lower end of the loosened region 152. A suture 100 is positioned through the ligament 150 and through the fasteners 30. The suture 100 is tensioned thereby tightening the loosened region 152 of the ligament 150.

In another embodiment, a fastener 30 is positioned against the ligament 150 above a stretched region 154. Another fastener 30 is placed against the ligament 150 below the stretched region 154. A suture 100 is placed through the ligament 150, adjacent vertebrae 156 and 158, and intervertebral disc 80 in a curved or looped configuration. The suture 100 is tensioned to tighten the stretched region 154.

In a further embodiment represented in FIG. 9, one fastener 30 is positioned against the ligament 150 above a missing or torn ligament region 160. Another fastener 30 is positioned against the ligament 150 below the missing region 160. The suture 100 is positioned through the superior and inferior ends of the ligament 150 at the missing or torn region 160. The suture 100 is tensioned between the fasteners 30 causing the ends of the ligament 150 to be drawn together.

To stabilize the spine while a loosened or torn ligament heals, a stabilization implant, such as a rod or plate 162, may be positioned adjacent spinous processes 164. The fasteners and sutures of the present invention may be used to secure the rod or plate 162 to the spine. A plurality of fasteners 30 is positioned against the rod or plate 162 proximate to each spinous process 164. A second plurality of fasteners 30 is placed within or against the spinous processes 164. Sutures 100 extend between the fasteners 30 and are tensioned. Once anchored, the rod or plate 162 limits movement of the spinous processes 164 relative to each other thereby limiting movement of the anterior longitudinal ligament 150.

It is contemplated that the fasteners of the present invention be placed within or adjacent any bone of the body. When used in the knee, for example, the fasteners may be placed adjacent the femur, tibia, or patella. Within the spine, an fastener may be positioned adjacent a posterior arch, a spinous process, a lateral or medial articular process, a pedicle, odontoid process, uncinate process, a posterior tubercle, carotid tubercle, or a vertebral body.

Example 5-Ligament Reconstruction

The present invention may also be used in ligament or tendon reconstruction. Ligaments are frequently damaged, detached, torn, or ruptured as the result of injury or surgery. A damaged ligament can impede proper motion of a joint and cause pain. Therefore, during or "on the way out" from a surgical procedure, a ligament may be reconstructed using a fastener, a tissue graft, and/or a tissue scaffold with or without cells.

The devices and methods of the present invention may be used with a tissue or artificial graft to tension and stabilize the damaged ligament. Any ligament of the body may be repaired using the present invention, including the ligaments of the spine, shoulder, elbow, hip, knee, ankle, feet, and hands. The present invention is described in reference to ligaments of the spine including the anterior and posterior longitudinal ligaments, interspinous ligaments, supraspinous ligaments, superior costotransverse ligaments, ligamentum flavum, facet capsulary ligament, intertransverse ligament, ligamentum nuchae, and ligaments of the sacrum and coccyx spine.

Figure 10:
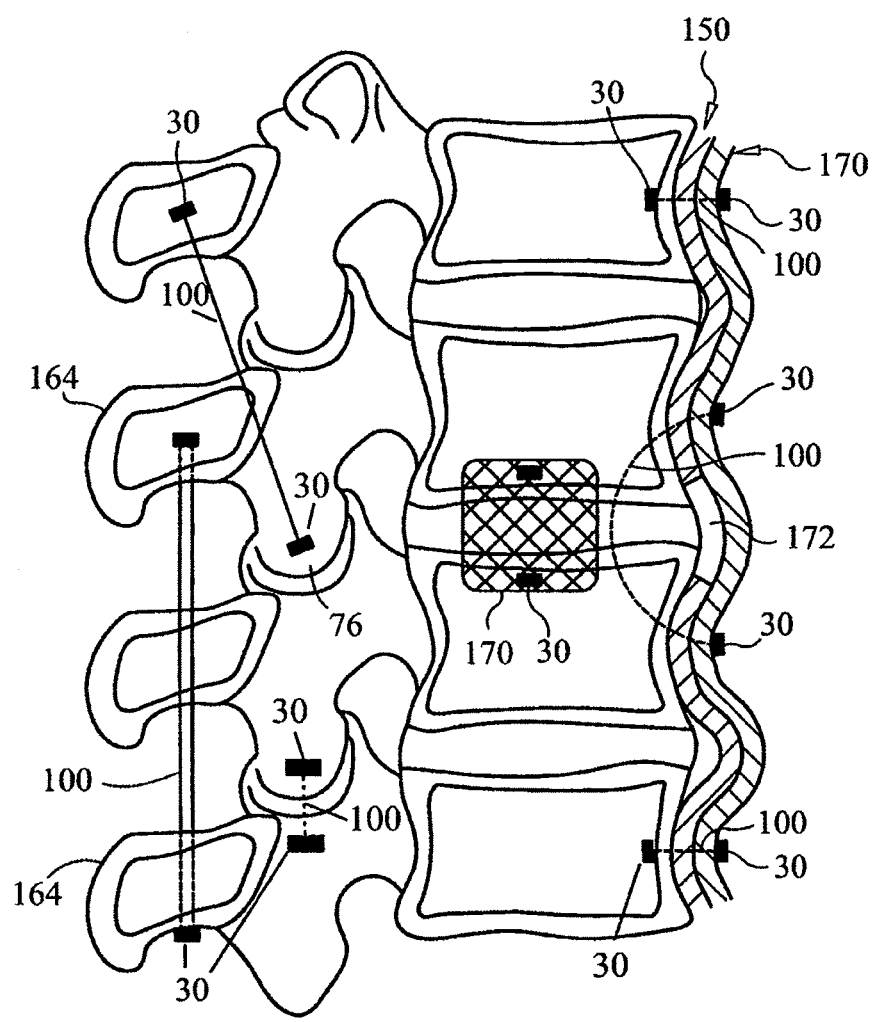
FIG. 10 shows ligament reconstruction and stabilization.

In an exemplary embodiment, FIG. 10 shows a damaged anterior longitudinal ligament 150. A ligament graft 170 is positioned adjacent the damaged region 172. A first fastener 30 is placed against the inferior end of the ligament graft 170, while a second fastener 30 is positioned within or against a vertebral body 174. A suture 100 extends through the graft 170, ligament 150, and vertebra 174. The suture 100 is tensioned, and the ends of the suture 100 are secured. Similarly, two fasteners and a suture are positioned at the superior end of the ligament graft. To further anchor the ligament graft 170 to the anterior longitudinal ligament 150, one fastener 30 is positioned against the graft 170 on one side of the damaged region 172, and another fastener 30 is placed against the graft 170 on the other side of the damaged region 172. A suture 100 is placed through the graft 170, ligament 150, adjacent vertebrae 82 and 84, and intervertebral disc 80 in a generally curved, looped, or C configuration. The suture 100 is tensioned, and the ends of the suture 100 secured. It is also contemplated that the curved or looped suture may be placed through multiple intervertebral discs and vertebrae.

In another embodiment, FIG. 10 shows a graft 170 positioned between two adjacent vertebrae 82 and 84. The ligament or bone graft 170 is positioned adjacent the damaged region 172 of the anterior longitudinal ligament 150. The graft 170 may be attached using any of the devices and methods described herein and incorporated by reference. In an exemplary embodiment, two fasteners 30 are placed at the superior and inferior ends of the graft 170. Two other fasteners (not shown) are positioned within or against each vertebra 82 and 84. Sutures are positioned between the fasteners and tensioned.

To stabilize the longitudinal ligament 150 while the damaged region 172 heals, sutures and fasteners may be placed on the posterior side of the spine for stabilization. One fastener 30 is placed within or against a spinous process 164, while another fastener 30 is positioned within or against a pedicle or bone of the facet joint 176. A suture 100 extends between the fasteners 30 thereby limiting movement of the spine. FIG. 10 shows an additional stabilization device between an upper and lower spinous process. In this configuration, the suture and fasteners provide additional restriction to the movement of the spine.

The ligament or bone graft may be obtained from a variety of sources and/or made from various materials. In an exemplary embodiment, the ligament graft is made of collagen. The graft could also include autograft, allograft, or xenograft material. The graft may be a tendon graft, bone-tendon-bone graft, or a meniscus graft. Other material which may be used in the formation of the graft is polymer, carbon fiber, PEEK, PTFE, a biodegradable material, elastic or flexible material, Gore-Tex®, or woven fiber. The ligament graft may include therapeutic substances. These include antibiotics, hydroxypatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Use of grafts or patches to repair, reconstruct, and augment tissue, like a ligament, may include patches such as TissueMend® patches, Restore® patches, or similar products.

Example 6-Ligament Augmentation

In addition to ligament repair and reconstruction, the devices and methods of the present invention may be used for ligament or tendon augmentation. Ligament augmentation reinforces or supplements natural ligaments. A ligament may be augmented or reinforced after it has been repaired or reconstructed. Also, a non-repaired ligament may be augmented prophylactically. In this case, the augmentation may be used to increase the load-bearing capacity of the ligament or tendon. Additionally, or alternatively, the augmentation may be used to prevent a potential injury to a ligament or tendon. For example, an athlete may undergo minimally invasive surgery to reinforce a ligament or tendon so as to prevent the ligament or tendon from being injured later in the athlete's career. Many talented athletes' careers are cut short because of any injury to a body joint, like the knee, shoulder, ankle, spine, wrist, or hip. If an athlete desired to prevent or at least reduce the chance of sustaining a career ending injury, he/she could have surgery to augment or "fail-safe" a joint and its ligaments and tendons even if there are no other risk factors other than the occupation. Of course, other risk factors, such as genetic predisposition, could be considered, if desired.

The devices and techniques described herein relate to augmenting any ligament or tendon of the body including ligaments of the knee, shoulder, spine, hand, foot, hip, and elbow. For illustrative purposes only, ligament augmentation is described with reference to the anterior cruciate ligament (ACL) of the knee. It should be understood that the description of augmentation to the knee is not limiting to other ligaments and tendons.

Figure 11:
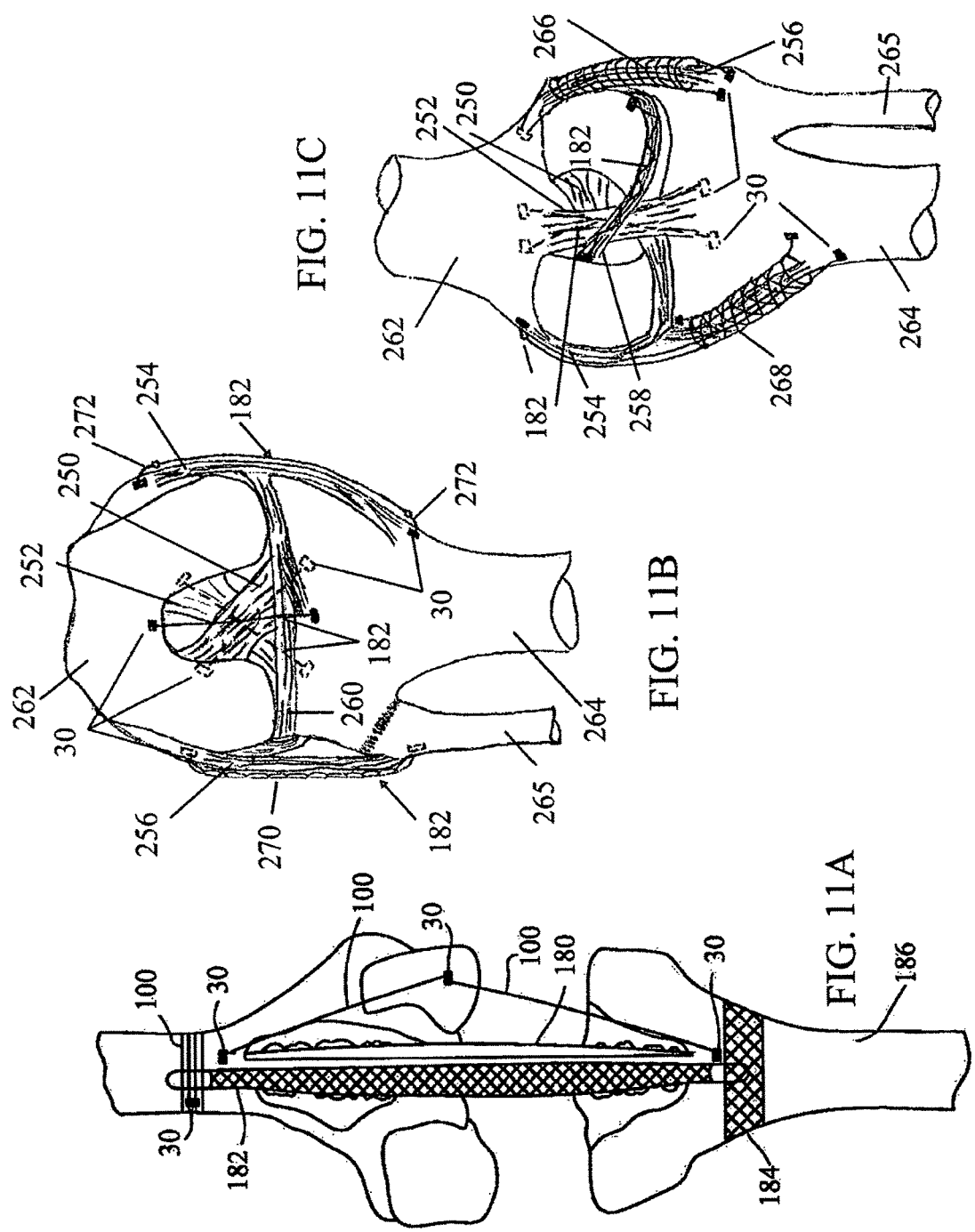
FIGS. 11A-11C illustrate ligament augmentation/reinforcement.

In an exemplary embodiment, fasteners and a suture (or similar device like a cable, band, flexible moment arm, pin, rod, or K-wire) may be used to augment a ligament. Referring to FIGS. 11A, 11B, and 11C, a fastener 30 may be positioned near one end of the ligament 180, while another fastener 30 may be placed near the opposite end of the ligament 180. The suture or cable 100 may be placed between the fasteners 30 and may be generally parallel with the ligament 180. The suture 100 may be tensioned, and the ends of the suture 100 secured with the fasteners 30. It is contemplated that multiple fasteners and multiple sutures may be utilized to augment the ligament. For example, a suture 100 may be placed at an angle to the ligament 180 with the ends of the suture 100 secured with fasteners 30. Having multiple sutures at different angles relative to each other and/or the ligament may provide multiple-direction augmentation.

In a further exemplary embodiment, a tissue graft or scaffold (reinforcement means) 182 may be used to augment the ligament or tendon 180. The graft or scaffold 182 may be configured and include materials as previously described herein. The graft or scaffold 182 may be positioned generally parallel to the ligament 180 requiring augmentation. The ends of the graft 182 may be anchored to bone, ligament, or other tissue using the devices and methods of the present invention. For example, one fastener may be positioned in or against the graft while another fastener may be placed in or against adjacent tissue. A suture may be tensioned between the fasteners, and the ends of the suture secured with the fasteners. Also, a fastener 30 may be positioned against the graft or adjacent tissue, and a suture 100 may be wrapped around the adjacent tissue and graft one or multiple times to form a band or latching. The suture 100 may be tensioned and secured with the fastener 30. It is contemplated that multiple grafts and/or scaffolds may be used to augment the ligament or tendon. For example, grafts or scaffolds may be at different angles to the ligament to provide augmentation in multiple directions.

Furthermore, it is contemplated that the graft or scaffold 182 used to augment the ligament or tendon may be secured to tissue using a band-like device 184. The band 184 may be wrapped around the graft or scaffold 182 and adjacent tissue, like a bone 186. The band 184 may be a biocompatible elastic band, a tissue graft, a polymeric or metallic tie (like a wire tie), or other suitable banding apparatus.

The suture and/or graft (reinforcement means) 182 used to augment the ligament or tendon may be placed parallel or diagonal to the ligament or tendon. Also, the suture and/or graft may be helically or spirally wrapped around the ligament or tendon. The ligament or tendon may be helically or spirally wrapped around the suture or graft. The reinforcement means may be positioned within or interwoven, braided, or weaved into the ligament or tendon.

As previously described, an athlete may desire to undergo elective surgery to "fail safe" a joint and/or ligaments. A football player, for example, who is at high risk for a knee injury may choose to augment or reinforce the anterior cruciate ligament 250, posterior cruciate ligament 252, tibial collateral ligament 254, fibular collateral ligament 256, posterior meniscofemoral ligament 258, and/or transverse ligament 260. The suture, cable, and/or graft used to reinforce the ligament may be tensioned and positioned such that the natural ligament is exclusively used during normal athletic activities. However, when the joint (knee) is extended or dislocated beyond its normal range of motion, the reinforcement means (suture, cable, graft, flexible rod, etc.) engages to stop the extension or dislocation thereby preventing injury to the joint. The engagement of the reinforcement means may provide a sudden stopping action when the joint or ligament is about to reach or has reached an abnormal position. Alternatively or additionally, the engagement of the reinforcement means may provide a gradual stopped action (e.g. stretching/elastic) as the joint/ligament approaches its maximum normal range.

The reinforcement means 182 may be implanted between bones, ligaments, and/or tendons. When the ACL is to be augmented or reinforced, the reinforcement means may extend between the femur 262, tibia 264, and/or fibula 265, may extend from the superior end of the ligament to the tibia and/or fibula, may extend from the inferior end of the ligament to the femur, and/or may extend between the superior and inferior ends of the ligament itself. The reinforcement means may be positioned parallel or at an angle to the ligament. The means may be a tubular sheath 266 that encapsulates the ligament, like a sheath on a wire or a braided sheath 268 on a fuel or hydraulic line. The sheath (reinforcement means) would function as previously described, i.e. provide gradual and/or sudden stopping action to the joint/ligament.

It is contemplated that augmentation or reinforcement of ligaments and tendons of a joint for athletes or other patients be performed using minimally invasive techniques. In the case of an athlete undergoing reinforcement or "fail safe" surgery, the surgeon must produce a minimum amount of dislocation and resection of soft tissue in order to minimize recovery time. Furthermore, physicians could take into consideration the natural growing rate of the athlete/patient. As the athlete grows and/or gains size and weight from physical workouts, the length, strength, and size of joints/ligaments/tendons may change. To account for this, the reinforcement means may be modifiable using a small portal in soft tissue to access the means in the joint. Once accessed, an extension 270 may be added to the reinforcement means. Alternatively, the reinforcement means may include three portions. The two end portions 272 may be fastened in tissue while the middle portion 274 resides between the end portions. The middle portion 274 may be disconnected from the end portions 272 and replaced with a different middle portion 274 having a different length, strength, and/or size. In this configuration, the end portions are not removed from the tissue therefore there is no healing time required for the end portions to secure to tissue.

Example 7-Laminectomy

A laminectomy is a surgical procedure which is designed to relieve pressure on the spinal cord or nerve root that is being caused by a slipped or herniated disk in the lumbar spine. A laminectomy removes a portion of bone over the nerve root or disc material from under the nerve root to give the nerve root more space and a better healing environment. Also, a laminectomy is effective to decrease pain and improve function for a patient with lumbar spinal stenosis. Spinal stenosis is caused by degenerative changes that result in enlargement of the facet joints. The enlarged joints place pressure on the nerves. During a laminectomy, there is much muscle stripping and ligament tearing. The back muscles or erector spinae are dissected off the lamina on both sides and at multiple levels. The facet joints, directly over the nerve roots, are cut to give the nerve roots space. Usually, once the nerve roots are provided with more room, the operation is completed by closing the skin incision. The methods and devices of the present invention may be used to repair, reconstruct, augment, and stabilize tissue or an implant "on the way out" of the pathway created in the soft tissue to access the nerve roots. Muscle may be reattached to muscle; ligaments may be repaired or reconstructed; tissue grafts may be implanted; bones may be stabilized; and implants may be inserted.

Figure 12:
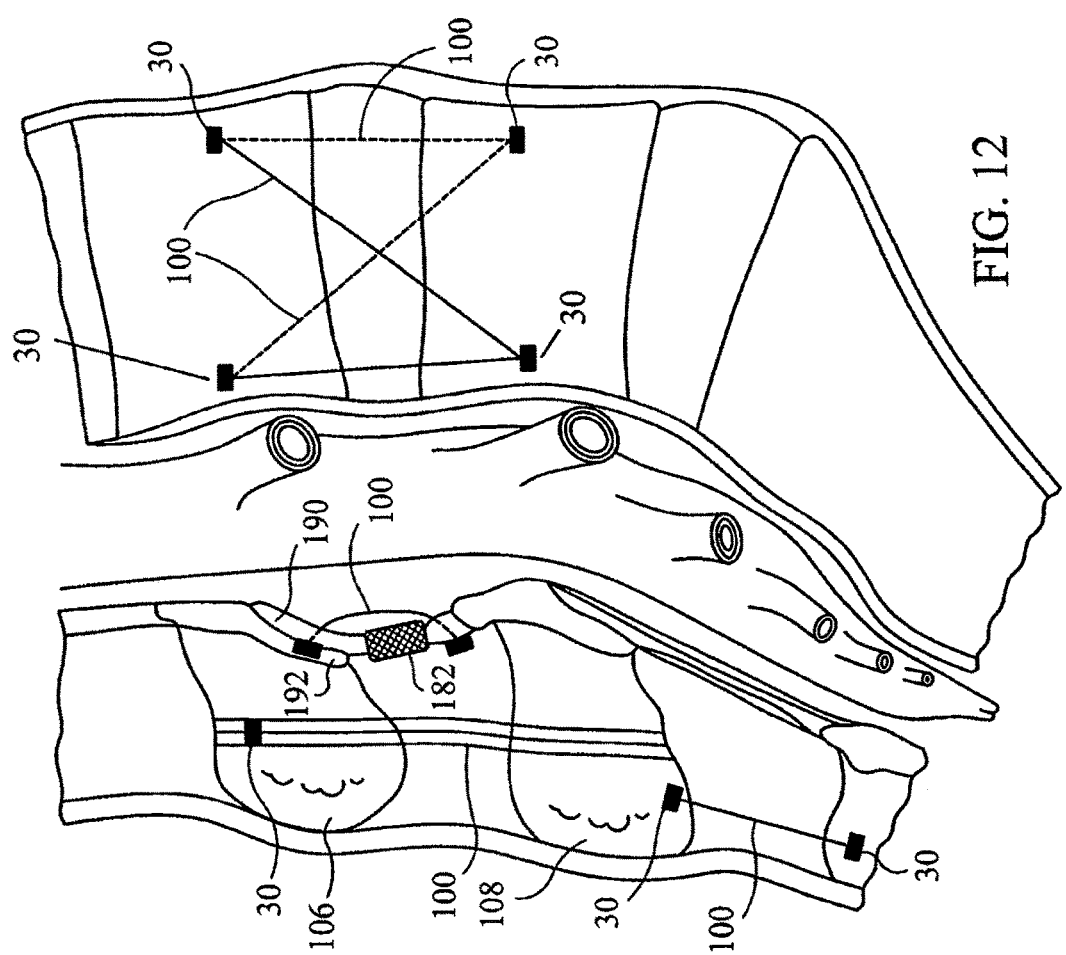
FIG. 12 shows a laminectomy site.

Referring to FIG. 12, a laminectomy site is illustrated. A portion of the ligamentum flavum 190 is dissected and removed between two spinous processes 106 and 108. The distal end of the lamina 192 is removed from the superior spinous process 106. The laminectomy site and surrounding tissue is repaired, reconstructed, or augmented to compress and stabilize the tissue for enhanced healing. Fasteners 30 and sutures or cables 100 are placed in the adjacent vertebral bodies 82 and 84 to provide flexible fixation of the spinal joint and limit the range of motion of the spine. A fastener 30 is positioned on the posterior side of the ligamentum flavum 190 above the laminectomy site. Another fastener 30 is positioned on the posterior side of ligamentum flavum 190 below the operation site. A suture 100 is placed between the fasteners 30. The suture 100 is tensioned and secured with the fasteners 30 to provide flexible fixation of the ligamentum flavum 190.

Another fixation device is placed between the inferior and superior spinous processes. A fastener 30 may be positioned against one of the spinous processes 164, and a suture 100 may be wrapped between two spinous processes 164. The suture 100 may be tensioned, and the ends of the suture 100 may be secured with the fastener 30. This configuration provides further flexible stabilization of the spinal column near the laminectomy site. Finally, a ligament graft or scaffold 182 may be positioned along the ligamentum flavum 190 over the laminectomy site. The graft 182 may reconnect and stabilize the ligamentum flavum 190. It should be understood that additional fasteners may be used to compress and stabilize surrounding tissue.

Example 8-Joint Stabilization

Following surgery within the body, especially surgery of a joint, the soft tissue around and near the joint may become weakened, and the range of motion of the joint usually increases thereby allowing excessive tissue laxity. Also, instability of a joint may be caused by structural changes within the joint as a result of trauma, degeneration, aging, disease, surgery, or a combinations thereof. An unstable joint may be fused to form a permanent or rigid internal fixation of all or part of the joint. Alternatively, joints may be stabilized with the devices and methods of the present invention, without fusion. In an exemplary embodiment, tissue may be repaired, reconstructed, augmented, and stabilized during and "on the way out" of a surgical procedure such as those surgical procedures described herein. Compressing and stabilizing the tissue around a joint enhances tissue healing. Using flexible fixation, the tissue may be secured but still allow for some range of motion of the joint. Where flexible fixation is not desired, the devices and methods of the present invention may be used for rigid fixation, such as for bones.

As a further example, fasteners and sutures could be used to stabilize the knee joint. The sutures could be positioned between at least two of the femur, tibia, patella, and adjacent ligaments to stabilize the knee without significantly restricting the knee's normal range of motion. Moreover, the devices and methods may be used to stabilize any joint of the body, including the spine, shoulder, elbow, wrist, hip, knee, ankle, and joints of the hands and feet. Additionally, the present invention may be used with a temporal mandibular joint, SI joint, facet joint, temporomandibular joint, and sacroiliac joint.

Figure 13:
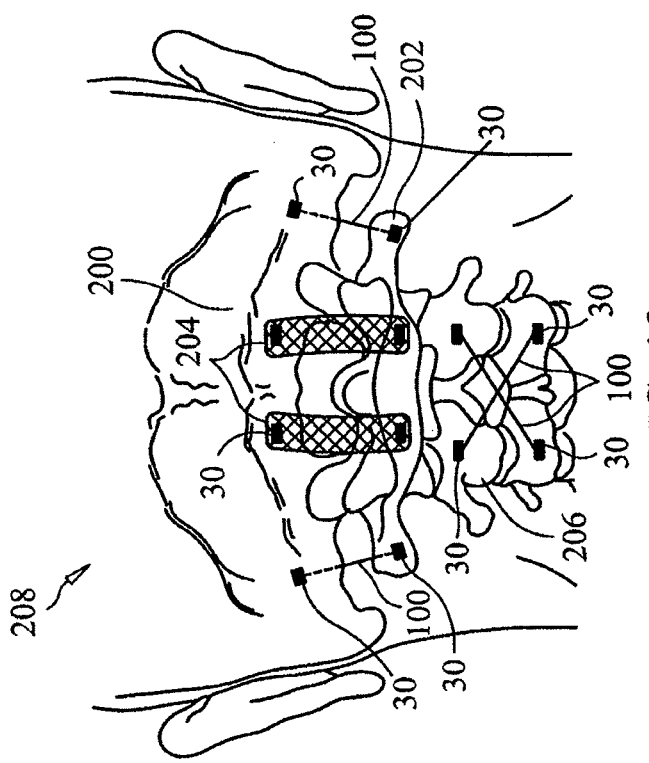
FIG. 13 illustrates stabilization of the cervical spine and head.

For illustrative purposes, the present invention is described in greater detail with respect to the spine. FIG. 13 shows a posterior view of the head and cervical spine with three vertebrae: C1 (Atlas), C2 (Axis), and C3. The cervical spine and head are stabilized using diagonally positioned sutures. Fasteners 30 are positioned within or against the left and right side of the occipital bone 200 of the head. Two other fasteners 30 are placed within or against the left and right sides of the posterior arch of the C1 vertebra 202. A suture 100 extends between the left fasteners 30, while another suture 100 extends between the right fasteners 30. When tensioned, the sutures 100 limit movement of the head relative to the cervical spine.

FIG. 13 also shows tissue graft 204, such as a ligament and/or bone graft, positioned between a vertebra 206 and the head 208. The grafts 204 may be attached using any of the devices and methods described herein and incorporated by reference. In an exemplary embodiment, fasteners 30 are placed at the superior and inferior ends of the graft. Other fasteners (not shown) are positioned within or adjacent the bone. Sutures extend between the fasteners and are tensioned.

Further stabilization of the cervical spine may be obtained by placing sutures and fasteners lower in the cervical spine. In an exemplary embodiment, a crisscross pattern of sutures is placed between two adjacent vertebrae. The upper fasteners 30 may be placed within or against the superior vertebra 82, while the lower fasteners 30 may be positioned within or against the inferior vertebra 84. Sutures 100 extend between the fasteners, and when tensioned, the sutures 100 stabilize the vertebrae 82 and 84 from movement between one another.

Figure 14:
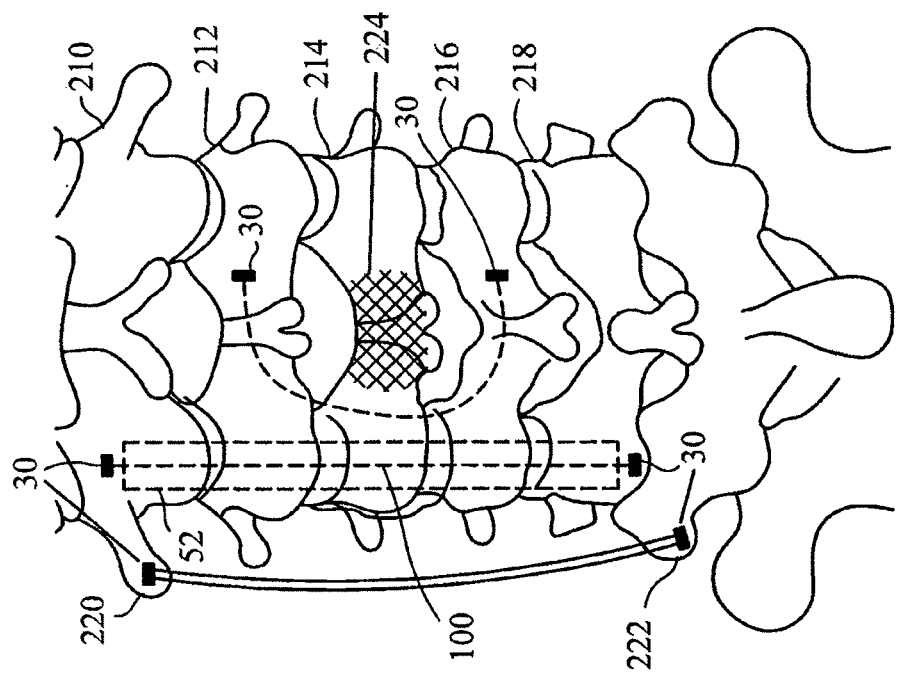
FIG. 14 shows decompression and stabilization of the spinal column.

In another embodiment as shown in FIG. 14, a vertebra 214 has been decompressed using fasteners and a suture. A first fastener 30 is placed within or adjacent an upper vertebra 212, and a second fastener 30 is positioned within or adjacent a lower vertebra 216. A suture 100 is positioned through the left side of the vertebrae 212, 214, and 216 in a curved, looped, or C configuration. The suture 100 is tensioned, and the ends of the suture 100 secured. By tensioning the suture 100, the right side of the middle vertebra 214 becomes decompressed.

In another exemplary embodiment, multiple vertebrae may be decompressed by positioning fasteners 30 on two vertebrae 210 and 218 which are separated by two or more vertebrae. A tubular member or sleeve 52 is positioned between the fasteners 30 and through the vertebrae in between. A suture 100 is placed within the sleeve 52, tensioned, and secured with the fasteners 30. Moreover, the fasteners 30 may be placed on any part/portion of the vertebrae 210 and 218, as described previously, so when the suture is tensioned, one or more vertebrae are decompressed, forming a decompressed region 224.

As further seen in FIG. 14, the spine has been stabilized using the pedicles of the spine. A fastener 30 is placed within or adjacent a pedicle 220. A second fastener 30 is placed within or adjacent another pedicle 222. A suture 100 extends between the fasteners 30 either through the pedicles or outside the pedicles. The suture 100 is tensioned and the ends of the suture secured.

While FIG. 14 illustrated a suture positioned between two pedicles, it is contemplated that the suture may be affixed to any portion/part of the vertebrae. For example, a suture may be tensioned between any one or more of the following: transverse process, pedicles, facets, spinous process, posterior arch, odontoid process, posterior tubercle, lateral articular process, uncinate process, anterior tubercle, carotid tubercle, and vertebral body.

The suture, or similar device like a cable, band, flexible moment arm, pin, rod, or K-wire, is made of a material having sufficient strength and fatigue characteristics. The suture may be biodegradable and/or flexible. It may include metallic material, ceramic material, polymeric material, composite material, or combinations thereof. In one embodiment, the suture is formed of fiber material like carbon or polyamide fibers. Sutures may also be formed from Mersilene®, polypropylene braided or collagen strips, allograft or xenograft strips, braided mesh, a polymer, PTFE, or Gore-Tex®. The suture may be made of or include an elastic, flexible material which stabilizes the skeletal and ligamentous system but allows some movement of the joints. Also, the suture may be barbed or could be a threaded wiring device.

The disclosed methods for spine stabilization described thus far included positioning fasteners against bone or an implant. However, the present invention also contemplates stabilizing a joint of the body by affixing a suture between ligaments, tendons, bones, cartilage, tissue grafts or combinations thereof. For example, a suture may be positioned between a vertebra and a longitudinal ligament, between a spinous process and the supraspinous ligament, or between a facet and a facet capsulary ligament. Any combination of attachment points is contemplated to stabilize the joint.

Furthermore, any of the methods described herein could utilize a plurality of sutures and more than two fasteners. The use of multiple sutures can vary the tension or resistance between the fasteners securing the suture, thereby providing various levels of stability. The use of multiple fasteners, preferably spaced apart and positioned adjacent the region of the joint to be stabilized, could provide various angles of stabilization.

It is further contemplated that by using multiple sutures and fasteners at different locations of the spine, ligaments and bones of the spine may be selectively tightened or stabilized to provide a customized environment for spine healing. For example, the sutures may be tightened sequentially between the fasteners, or the entire construct could be tightened down together.

RELATED TECHNIQUES

It is contemplated that the devices and methods of the present invention be applied using minimally invasive incisions and techniques to preserve muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled, Expandable Cannula Having Longitudinal Wire and Method of Use, discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

In addition to using a cannula with the methods of the present invention, an introducer may be utilized to position fasteners at a specific location within the body. U.S. Pat. No. 5,948,002 entitled, Apparatus and Method for Use in Positioning a Suture Anchor, discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VersaStep® System by Tyco® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

Moreover, the devices and methods of the present invention may by used to approximate a skin incision where there may be undue tension on the skin. Fasteners may be placed on opposite sides of the incision, and a suture or cable may be placed between the fasteners. When the suture is tensioned, the skin may be pulled together and held until the skin tissue relaxes. Then, the fasteners may be unlocked, and the suture may be tensioned again to further approximate the skin incision. The locking and unlocking of the fasteners along with the tensioning of the suture may be repeated until the incision is fully closed.

Furthermore, it is contemplated that the present invention may be used with bariatric surgery, colorectal surgery, plastic surgery, gastroesophageal reflex disease (GERD) surgery, or for repairing hernias. A band, mesh, or cage of synthetic material or body tissue may be placed around an intestine or other tubular body member. The band may seal the intestine. This method may be performed over a balloon or bladder so that anastomosis is maintained. The inner diameter of the tubular body part is maintained by the balloon. The outer diameter of the body part is then closed or wrapped with a band, mesh, or patch. The inner diameter of the tubular body member may be narrowed or restricted by the band. The band may be secured to the tubular body part or surrounding tissue with the devices and methods described herein and incorporated by reference.

In addition, intramedullary fracture fixation and comminuted fracture fixation may be achieved with the devices and methods of the present invention. For example, a plate or rod may be positioned within or against the fractured bone. A fastener may be driven across the bone and locked onto the plate, rod, or another fastener.

It is further contemplated that the present invention may be used in conjunction with the devices and methods disclosed in U.S. Pat. No. 5,329,846 entitled, Tissue Press and System, and U.S. Pat. No. 5,269,785 entitled, Apparatus and Method for Tissue Removal. For example, an implant secured within the body using the present invention may include tissue harvested, configured, and implanted as described in the patents. The above-mentioned patents are hereby incorporated by reference.

Additionally, it is contemplated that the devices and methods of the present invention may be used with heat bondable materials as disclosed in U.S. Pat. No. 5,593,425 entitled, Surgical Devices Assembled Using Heat Bondable Materials. For example, the fasteners of the present invention may include heat bondable material. The material may be deformed to secure tissue or hold a suture or cable. The fasteners made of heat bondable material may be mechanically crimped, plastically crimped, or may be welded to a suture or cable with RF (Bovie devices), laser, ultrasound, electromagnet, ultraviolet, infrared, electro-shockwave, or other known energy. The welding may be performed in an aqueous, dry, or moist environment. The welding device may be disposable, sterilizable, single-use, and/or battery-operated. The above-mentioned patent is hereby incorporated by reference.

Furthermore, it is contemplated that the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

Moreover, the fasteners and methods of the present invention may be used for the repair and reconstruction of a tubular pathway like a blood vessel, intestine, urinary tract, esophagus, or other similar body parts. For example, a blood vessel may be intentionally severed during a surgical operation, or the blood vessel may be damaged or torn as a result of an injury. Flexible fixation of the vessel would permit the vessel to function properly and also compress and stabilize the vessel for enhanced healing. To facilitate the repair or reconstruction of a body lumen, a balloon may be inserted into the lumen and expanded so the damaged, severed, or torn portion of the vessel is positioned against the outer surface of the inflated balloon. In this configuration, the fasteners and methods described and incorporated herein may be used to approximate the damaged portion of the vessel.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

I claim:

1. A surgical method for ligament augmentation comprising:
   securing a first fastener at least partially within a first bone of a joint adjacent a first end of a ligament of the joint, wherein the first end of the ligament is attached to the first bone of the joint before securing the first fastener, and wherein a reinforcement component comprised of a multifilament structure fabricated from polyethylene and polyester is attached directly to the first fastener to anchor the reinforcement component to the first bone; and
   securing a second fastener at least partially within a second bone of a joint adjacent a second end of the ligament of the joint opposite the first end of the ligament, wherein the second end of the ligament is attached to the second bone of the joint before securing the second fastener, and wherein the reinforcement component is attached to the second fastener to anchor the reinforcement component to the second bone,
   wherein the reinforcement component extends between the first and second ends of the ligament, and
   wherein the reinforcement component is tensioned directly between the first and second fasteners.

2. The surgical method for ligament augmentation set forth in claim 1, wherein the reinforcement component extends along the length of the ligament.

3. The surgical method for ligament augmentation set forth in claim 1, wherein the reinforcement component comprises a suture.

4. The surgical method for ligament augmentation set forth in claim 3, wherein the reinforcement component comprises a plurality of sutures.

5. The surgical method for ligament augmentation set forth in claim 1, wherein the first and second bones and the joint are part of a foot.

6. The surgical method for ligament augmentation set forth in claim 1, wherein the first and second bones and the joint are part of a knee.

7. The surgical method for ligament augmentation set forth in claim 1, wherein the first and second bones and the joint are part of a shoulder.

8. The surgical method for ligament augmentation set forth in claim 1, wherein the first and second bones and the joint are part of a spine.

9. The surgical method for ligament augmentation set forth in claim 1, wherein the first and second bones and the joint are part of a hand.

10. The surgical method for ligament augmentation set forth in claim 1, wherein the first and second bones and the joint are part of a hip.

11. The surgical method for ligament augmentation set forth in claim 1, wherein the first and second bones and the joint are part of an elbow.

12. The surgical method for ligament augmentation set forth in claim 1, wherein the reinforcement component is configured to prevent dislocation of the joint.

* * * * *

(12) INTER PARTES REVIEW CERTIFICATE (3382nd)
United States Patent (10) Number: US 9,999,449 K1
Bonutti (45) Certificate Issued: Jan. 23, 2024

(54) DEVICES AND METHODS FOR STABILIZING TISSUE AND IMPLANTS

(71) Applicant: Peter M. Bonutti

(72) Inventor: Peter M. Bonutti

(73) Assignee: P TECH, LLC

Trial Number:

IPR2022-00787 filed Apr. 11, 2022

Inter Partes Review Certificate for:

Patent No.: 9,999,449
Issued: Jun. 19, 2018
Appl. No.: 14/205,442
Filed: Mar. 12, 2014

The results of IPR2022-00787 are reflected in this inter partes review certificate under 35 U.S.C. 318(b).

INTER PARTES REVIEW CERTIFICATE
U.S. Patent 9,999,449 K1
Trial No. IPR2022-00787
Certificate Issued Jan. 23, 2024

AS A RESULT OF THE INTER PARTES REVIEW PROCEEDING, IT HAS BEEN DETERMINED THAT:

Claims 1-11 are cancelled.

\* \* \* \* \*